(12) United States Patent
Luttringer et al.

(10) Patent No.: US 8,497,103 B2
(45) Date of Patent: Jul. 30, 2013

(54) METHODS FOR C4-DICARBOXYLIC ACID PRODUCTION IN FILAMENTOUS FUNGI

(75) Inventors: Sheryl Luttringer, Loomis, CA (US); Debbie Yaver, Davis, CA (US)

(73) Assignee: Novozymes, Inc., Davis, CA (US)

( * ) Notice: Subject to any disclaimer, the term of this patent is extended or adjusted under 35 U.S.C. 154(b) by 88 days.

(21) Appl. No.: 13/165,719

(22) Filed: Jun. 21, 2011

(65) Prior Publication Data

US 2011/0312046 A1 Dec. 22, 2011

Related U.S. Application Data

(60) Provisional application No. 61/357,007, filed on Jun. 21, 2010.

(51) Int. Cl.
*C12N 1/15* (2006.01)
*C12P 7/46* (2006.01)

(52) U.S. Cl.
USPC ........................................ 435/145; 435/254.3

(58) Field of Classification Search
None
See application file for complete search history.

(56) References Cited

U.S. PATENT DOCUMENTS

| 3,063,910 A | 11/1962 | Abe et al. |
| 5,536,661 A | 7/1996 | Boel et al. |
| 7,504,490 B1 | 3/2009 | Weinstock et al. |

FOREIGN PATENT DOCUMENTS

| EP | 2471943 A1 | 7/2010 |
| WO | WO 2007-061590 A1 | 5/2007 |
| WO | WO 2008-144626 A1 | 11/2008 |
| WO | WO 2009/011974 A1 | 1/2009 |
| WO | WO 2009-065778 A1 | 5/2009 |
| WO | WO 2009-155382 A1 | 12/2009 |
| WO | WO 2010-003728 A1 | 1/2010 |
| WO | WO 2010-111344 A2 | 9/2010 |
| WO | 2011024583 A1 | 3/2011 |
| WO | WO2011028643 A1 | 3/2011 |
| WO | 2011066304 A2 | 6/2011 |

OTHER PUBLICATIONS

GenBank Accession No. XM_00127657. (Feb. 2008).*
D. Lubertozzi et al. "Developing *Aspergillus* as a Host for Heterologous Expression", Biotechnology Advances 27:53-75. (Sep. 2008).*
J.C. Whisstock et al. "Prediction of Protein Function From Protein Sequence and Structure", Quarterly Review of Biophysics 36(3):307-340 (2003).*
Machida et al 2006, UniProt Access No. Q2UGL1.
Machida et al 2006, UniProt Access No. Q2USG33.
Birren et al, 2008, UniProt Access No. B6JXU3.
Elleuche et al, 2009, Curr Genet 55, 211-222.
Fedorova et al, 2007, UniProt Access No. A1C406.
Goldberg et al, 2006, J Chem Technol Biotechnol 81(10), 1601-1611.
Nevoigt, 2008, Microbiol Mol Biol Revs 72(3), 379-412.
Nielsen et al, 2008, FEMS Yeast Res 8, 122-131.
Geneseq, Access No. AWP70496, Oct. 2010.
Geneseq, Access No. ATT44026, Apr. 2009.
Battat et al, 1991, Biotechnol Bioeng 37, 1108-1116.
Nierman et al, 2005, UniProt Access No. Q4WCF3.
Battat 1991, Biotechnol Bioeng 37, 1108-1116.
Bauer 1999, FEMS Microbial Lett 179, 107-113.
Bercovitz 1990, Appl Environ Microbiol 56, 1594-1597.
Camarasa 2001, Appl Environ Microbiol 67(9), 4144-4151.
Fedorova 2008, PLoS Genetics 4(4), 1-13.
Grobler 1995, Yeast 11, 1485-1491.
Nierman 2005, Nature 438 (22).
Peleg 1988, Appl Microbiol Biotechnol 28, 69-75.
Pines 1997, Appl Microbiol Biotechnol 48, 248-255.
Sauer 2008, Trends Biotechnol 26, 100-108.
Zelle 2008, Appl Environ Microbiol 74, 2766-2777.
Zelle, Rintze Meindert. Metabolic engineering of *Saccharomyces cerevisiae* for C4-dicarboxylic acid production. PhD Thesis. Delft Univerisy of Technology, Delft, 2011.
Ludwig et al, 1998, Plant Physiol 117 (3), 1071-1081.
WO 2011-024583—Eng Equiv—EP 2 471 943.

* cited by examiner

*Primary Examiner* — Rebecca Prouty
(74) *Attorney, Agent, or Firm* — Eric J. Fechter

(57) ABSTRACT

The present invention relates to methods of producing C4-dicarboxylic acids, such as malic acid, comprising: (a) cultivating a host cell comprising a polynucleotide encoding a C4-dicarboxylic acid transporter; and (b) recovering the C4-dicarboxylic acid. The present invention also relates to methods for increasing C4-dicarboxylic acid production, as well as host cells comprising the polynucleotides.

18 Claims, 10 Drawing Sheets

```
          M   F   E   N   R   I   P   P   T   S   S   Q   S   D   S   G   F   L   E   N
   1 ATGTTCGAAA ATCGTATACC GCCGACCTCG TCTCAGTCAG ACTCTGGCTT CCTCGAGAAC
       Q   L   E   K   Q   H   R   L   S   L   R   E   R   L   R   H   F   T   W   A
  61 CAGCTGGAAA AACAACATCG ACTCAGCCTC CGTGAGAGGT TAAGGCACTT TACCTGGGCC
       W   Y   T   L   T   M   S   T   G   G   L   A   L   L   I   A   S   Q   P   Y
 121 TGGTACACAT TGACCATGAG CACAGGTGGG TTGGCTCTCC TGATAGCGAG CCAGCCATAC
       T   F   K   G   L   K   T   I   G   L   V   V   Y   I   V   N   L   I   L   F
 181 ACCTTCAAGG GGTTGAAGAC CATTGGACTG GTGGTCTACA TCGTGAACTT GATCTTGTTT
       G   L   V   C   S   L   M   A   T   R   F   I   L   H   G   G   F   L   D   S
 241 GGTCTTGTCT GTTCCCTTAT GGCCACTAGG TTCATCCTCC ACGGTGGCTT CCTCGACTCC
       L   R   H   E   R   E   G   L   F   F   P   T   F   W   L   S   V   A   T   I
 301 CTTCGCCATG AGCGCGAGGG TCTTTTCTTT CCTACCTTCT GGCTATCCGT AGCAACCATC
       I   T   G   L   H   R   Y   F   G   S   D   A   R   E   S   Y   L   I   A   L
 361 ATCACCGGCT TGCATCGCTA CTTCGGCTCC GATGCTCGAG AATCGTACCT GATTGCACTC
       E   V   L   F   W   V   Y   C   A   C   T   L   A   T   A   V   I   Q   Y   S
 421 GAAGTACTCT TCTGGGTCTA CTGTGCCTGT ACACTGGCCA CAGCAGTGAT CCAGTACTCC
       F   I   F   S   A   H   R   Y   G   L   Q   T   M   M   P   S   W   I   L   P
 481 TTCATCTTCT CTGCGCACAG ATACGGCCTC CAGACCATGA TGCCCTCCTG GATTCTCCCA
       A   F   P   I   M   L   S   G   T   I   A   S   V   I   G   E   A   Q   P   A
 541 GCCTTCCCCA TCATGCTCAG TGGCACGATT GCCTCCGTCA TCGGCGAAGC TCAACCCGCA
       R   S   S   I   P   V   I   M   A   G   V   T   F   Q   G   L   G   F   S   I
 601 CGGTCATCGA TCCCCGTCAT CATGGCCGGA GTCACCTTCC AGGGCCTGGG GTTCTCGATC
       S   F   M   M   Y   A   H   Y   I   G   R   L   M   E   S   G   L   P   C   R
 661 AGCTTCATGA TGTACGCCCA CTATATCGGC CGGCTGATGG AATCAGGGCT CCCCTGCCGC
       E   H   R   P   G   M   F   I   C   V   G   P   P   A   F   T   A   L   A   L
 721 GAGCACAGAC CCGGCATGTT CATCTGCGTT GGTCCCCCGG CTTTCACAGC CCTCGCTCTA
       V   G   M   A   K   G   L   P   A   E   F   K   L   I   N   D   A   H   A   L
 781 GTCGGGATGG CCAAGGGCCT GCCCGCCGAG TTCAAGCTCA TCAACGACGC ACACGCCCTC
       E   D   A   R   I   L   E   L   L   A   I   T   A   G   I   F   L   W   A   L
 841 GAAGACGCGC GGATCCTCGA GCTGCTCGCA ATCACCGCGG GCATCTTCCT CTGGGCCCTG
       S   L   W   F   F   I   A   V   I   A   V   L   R   S   P   P   T   S   F
 901 AGTCTGTGGT TCTTCTTCAT CGCCGTCATC GCCGTCCTCC GGTCCCCGCC TACTTCCTTC
       H   L   N   W   A   L   V   F   P   N   T   G   F   T   L   A   T   I   T
 961 CATCTCAACT GGTGGGCCTT GGTCTTCCCG AACACGGGCT TCACTTTGGC CACCATCACG
       L   G   K   A   L   G   S   P   G   I   L   G   V   G   S   A   M   S   L   G
1021 CTTGGAAAGG CATTGGGCAG TCCCGGGATC TTGGGCGTTG GTTCTGCCAT GTCCCTTGGC
       I   V   G   M   W   L   F   V   F   V   S   H   I   R   A   I   I   N   Q   D
1081 ATCGTTGGCA TGTGGCTGTT TGTTTTTGTC AGCCATATCC GTGCCATCAT CAACCAGGAT
       I   M   Y   P   G   K   D   E   D   A   A   D   *
1141 ATCATGTATC CGGGCAAAGA TGAGGATGCT GCAGACTAG
```

Fig. 4

```
         M   F   N   D   H   D   H   V   P   P   T   S   S   Q   S   D   S   G   F   F
   1 ATGTTCAACG ATCATGATCA TGTTCCACCA ACATCATCAC AGTCGGATTC TGGCTTTTTT
     E   Q   E   M   K   K   S   P   R   L   S   L   R   E   R   L   R   H   F   T
  61 GAACAAGAAA TGAAGAAATC TCCTCGACTA AGCCTTCGTG AGCGCCTACG GCACTTCACC
     W   A   W   Y   T   L   T   M   S   T   G   G   L   A   L   L   I   A   S   Q
 121 TGGGCGTGGT ATACCTTGAC GATGAGTACC GGTGGACTGG CTCTTCTGAT TGCTAGTCAG
     P   Y   T   F   N   G   M   K   G   I   G   M   V   V   Y   I   L   N   L   L
 181 CCGTATACCT TCAATGGCAT GAAGGGCATC GGGATGGTCG TTTATATCCT CAATCTTCTG
     L   F   A   L   V   C   S   L   M   V   L   R   F   V   L   H   G   G   F   L
 241 TTATTCGCTC TTGTCTGTTC TTTGATGGTG CTGAGATTCG TTTTGCATGG CGGTTTCCTT
     D   S   L   R   H   P   R   E   G   L   F   F   P   T   F   W   L   S   I   A
 301 GACAGCTTGC GCCACCCTCG CGAGGGTCTC TTCTTCCCTA CCTTCTGGCT ATCCATTGCA
     T   I   I   T   G   L   H   R   Y   F   G   S   D   D   L   E   S   Y   L   I
 361 ACGATCATCA CTGGCTTGCA TCGTTACTTC GGCTCCGACG ACCTAGAGTC GTACCTCATC
     A   L   E   V   L   F   W   V   Y   C   S   C   T   L   A   T   A   V   I   Q
 421 GCACTCGAAG TCCTCTTCTG GGTCTACTGT AGTTGCACCC TCGCCACAGC TGTGATCCAG
     Y   S   F   L   F   A   A   H   S   Y   G   L   Q   T   M   M   P   S   W   I
 481 TACTCATTCC TCTTTGCCGC CCACTCCTAC GGCCTGCAGA CAATGATGCC ATCATGGATC
     L   P   A   F   P   I   M   L   S   G   T   I   A   S   V   I   S   E   S   Q
 541 CTACCAGCCT TCCCCATCAT GCTCAGCGGA ACCATCGCCT CGGTCATCAG CGAATCCCAG
     P   A   R   S   A   I   P   I   I   T   A   G   V   T   F   Q   G   L   G   F
 601 CCCGCGCGAT CCGCGATCCC CATCATCACT GCCGGCGTTA CCTTCCAGGG CCTCGGCTTC
     S   I   S   F   I   M   Y   A   H   Y   I   G   R   L   M   Q   S   G   L   P
 661 TCAATCAGCT TCATAATGTA CGCCCACTAC ATCGGCCGAC TCATGCAGTC AGGGCTTCCC
     C   R   E   H   R   P   A   M   F   I   C   V   G   P   P   S   F   T   A   L
 721 TGCCGCGAAC ACAGACCAGC CATGTTCATT TGCGTGGGGC CTCCGTCTTT CACCGCGTTG
     A   L   V   G   M   A   K   G   L   P   D   E   F   K   I   I   K   D   A   H
 781 GCGCTAGTAG GGATGGCCAA GGGCCTGCCC GACGAATTCA AGATAATCAA AGACGCACAC
     V   E   D   A   R   I   L   E   L   M   A   I   I   V   G   V   F   L   W   A
 841 GTCGAGGACG CCCGGATCCT CGAGCTGATG GCTATTATCG TCGGCGTGTT CCTGTGGGCC
     L   S   L   W   F   F   F   I   A   F   V   A   V   V   R   C   R   P   T   A
 901 CTGAGTCTCT GGTTCTTCTT CATTGCCTTT GTTGCTGTCG TCCGGTGCCG GCCCACTGCG
     F   H   L   S   W   W   A   M   V   F   P   N   T   G   F   T   L   A   T   I
 961 TTCCACCTTA GCTGGTGGGC CATGGTCTTC CCCAACACTG GGTTCACGCT GGCCACTATT
     T   L   G   R   A   L   G   S   P   G   V   L   G   V   G   S   A   M   S   V
1021 ACCCTGGGGA GGGCATTGGG GAGCCCTGGC GTCTTGGGCG TCGGCTCGGC CATGTCGGTC
     G   V   V   C   M   W   V   F   V   F   V   Y   H   I   R   A   V   I   R   Q
1081 GGTGTTGTCT GCATGTGGGT CTTCGTTTTC GTCTACCACA TTCGTGCTGT CATCAGGCAA
     D   I   M   Y   P   G   K   D   E   D   V   L   D   *
1141 GACATCATGT ACCCGGGCAA AGACGAGGAT GTGCTAGATT AA
```

Fig. 7

```
      M  V  K  A
  1 ATGGTCAAAG CTGGTGAGTT AGCAATCCTT AACAGATGAC ACTCTCATAG GTACTAACTC
             A  V  L  G  A  S  G    G  I  G  Q
 61 GAAACGTTAG CGGTACTTGG AGCTTCTGGT GGCATTGGCC AGGTATGGAT ATCCCCACGC
                                                           P  L  S ·
121 CTTACAACCC TGGTCACAAT ATGACCTTGT TCGATACTGA CTATCTCCCA AGCCACTGTC
  · L  L  L  K  T  C  P  L  V  E    E  L  A  L  Y  D  V  V  N  T ·
181 TCTCCTGTTG AAGACCTGTC CCTTAGTTGA AGAGCTTGCT CTCTACGATG TTGTGAACAC
  · P  G  V  A  A  D  L  S  H  I    S  S  I  A
241 CCCTGGTGTT GCTGCTGATC TATCCCACAT CTCGTCTATC GCTGTACGTT ACTGCCACAA
                                                                 K
301 TGCGAATTGC CCGATGGAAG AGGCGAAAAA TGGTATCTTG CTTACCTGGG CGATTAGAAA
       I  S  G  F  L  P  K  D  D    G  L  K  Q  A  L  T  G  A  N  I
361 ATCTCTGGTT TTCTGCCCAA AGATGATGGG CTGAAGCAGG CCCTTACTGG TGCTAATATT
       V  V  I  P  A  G  I  P
421 GTTGTCATCC CGGCTGGTAT TCCCCGTAAG TCCCTACCCT TCGCATTGCC TCCTCGTATG
                                                 R  K  P  G  M  T  R  D  D  L ·
481 TTCGCTGGTG CCAGTTTTC TGATAGTTGA TAGGCAAGCC TGGTATGACC CGTGACGACC
  · F  K  I  N  A  G  I  V  R  D    L  V  K  G  I  A  E  F  C  P ·
541 TCTTCAAGAT CAACGCCGGC ATAGTGCGAG ACTTGGTCAA GGGTATCGCC GAGTTCTGCC
  · K  A  F  V  L  V  I  S  N  P    V  N  S  T  V  P  I  A  A  E ·
601 CCAAGGCCTT TGTTCTGGTT ATCTCAAACC CCGTTAATTC TACTGTTCCT ATTGCTGCAG
  · V  L  K  A  A  G  V  F  D  F    K  R  L  F  G  V  T  T  L  D ·
661 AGGTGCTCAA AGCCGCTGGC GTCTTTGACC CGAAGCGCCT CTTTGGTGTC ACCACACTGG
  · V  V  R  A  E  T  F  T  Q  E    F  S  G  Q  K  D  P  S  A  V ·
721 ACGTCGTTCG TGCAGAGACT TTCACCCAAG AGTTCTCGGG CCAGAAGGAT CCTTCTGCTG
  · Q  I  P  V  V  G  G  H  S  G    E  T  I  V  P  L  F  S  K  T ·
781 TTCAAATCCC AGTTGTTGGT GGCCACTCTG GAGAGACCAT TGTCCCCCTC TTCAGCAAGA
  · T  P  A  I  Q  I  P  E  E  K    Y  D  A  L  I  H
841 CTACCCCCGC AATTCAGATA CCCGAGGAGA AGTATGACGC ACTGATCCAC CGTAGGTTGT
                                                      R  V  Q  F
901 CCCAAAGAAT CTCATGAATA TCTTGCTGTA AGCACTAACT ATGCTTCAGG CGTCCAATTT
       G  D  E  V  V  Q  A  K  D    G  A  G  S  A  T  L  S  M  A
961 GGTGGAGATG AGGTGGTCCA AGCTAAGGAC GGTGCTGGTT CCGCCACCTT GTCTATGGCC
       Y  A  G  Y
1021 TATGCCGGTT ACAGGTAGGG ATGCTGCGTA CCGTGAGAGC ACTCGCGGCT AACATGCCAT
       R  F  A  E  S  V  I  K  A    S  K  G  Q  T  G  I  V  E  P  T
1081 AGGTTCGCTG AGAGTGTAAT CAAAGCTTCA AAGGGTCAAA CGGGTATTGT CGAGCCTACC
       F  V  Y  L  P  G  I  P  G    G  D  E  I  V  K  A  T  G  V  E
1141 TTCGTCTACC TGCCTGGAAT TCCCGGCGGT GATGAGATCG TTAAGGCAAC TGGCGTGGAA
       F  F  S  T  L  V  T  L  G
1201 TTCTTCTCTA CTCTTGTAAC CTTAGGAGTA AGATTCATCT CCTCACAGAA TCTTCGTTCA
                                               T  N  G  A  E  K  A  S  N  V  L ·
1261 TATCACGCCA GGCTAACGCT ATTAAACAGA CTAATGGCGC AGAGAAGGCT AGCAACGTTC
  · E  G  V  T  E  K  E  K  K  L    L  E  A  C  T  K  G  L  K  G ·
1321 TTGAGGGCGT GACCGAGAAG GAAAAGAAGC TTCTCGAGGC TTGCACGAAA GGCCTTAAGG
  · N  I  E  K  G  I  D  F  V  K    N  P  P  P  K  *
1381 GTAATATCGA GAAAGGCATC GACTTCGTTA AGAACCCACC ACCAAAGTAA
```

Fig. 8

```
            M   A   A   P       F   R   Q       P   E   E       A   V   D   D       T   E   F       I   D   D
   1    ATGGCGGCTC CGTTTCGTCA GCCTGAGGAG GCGGTCGATG ACACCGAGTT CATCGATGAC
            H   H   E   H       L   R   D       T   V   H       H   R   L       R   A   N   S       S   I   M
  61    CACCATGAAC ACCTCCGTGA TACCGTGCAC CATCGGTTGC GCGCCAATTC CTCCATTATG
            H   F   Q   K       I   L   V       A   N   R       G   E   I       P   I   R   I       F   R   T
 121    CACTTCCAGA AGATCCTCGT CGCCAACCGT GGTGAGATCC CCATTCGTAT CTTCAGAACG
            A   H   E   L       S   L   Q       T   V   A       I   Y   S       H   E   D   R       L   S   M
 181    GCCCACGAGC TGTCCTTGCA GACGGTTGCT ATCTACTCTC ATGAGGATCG ACTGTCAATG
            H   R   Q   K       A   D   E       A   Y   M       I   G   H   R       G   Q   Y       T   P   V
 241    CACCGTCAAA GGCCGATGA GGCCTACATG ATTGGCCACC GCGGTCAGTA CACCCCTGTC
            G   A   Y   L       A   G   D       E   I   I       K   I   A       L   E   H   G       V   Q   L
 301    GGTGCGTACC TGGCGGGCGA TGAGATCATC AAGATCGCCC TGGAGCACGG TGTCCAGCTG
            I   H   P   G       Y   G   F       L   S   E       N   A   D       F   A   R   K       V   E   N
 361    ATCCACCCGG GCTACGGTTT CTTGTCCGAG AACGCCGACT TCGCCCGCAA GGTTGAGAAC
            A   G   I   V       F   V   G       P   T   P       D   T   I       D   S   L   G       D   K   V
 421    GCCGGCATTG TCTTTGTGGG ACCCACTCCC GATACCATTG ACAGCTTGGG TGACAAGGTG
            S   A   R   R       L   A   I       K   C   E       V   P   V       V   P   G   T       E   G   P
 481    TCGGCCCGTC GGCTGGCCAT TAAGTGCGAG GTCCCTGTCG TTCCGGGTAC GGAGGGCCCC
            V   E   R   Y       E   E   V       K   A   F       T   D   T   Y       G   F   P       I   I   I
 541    GTCGAGCGCT ATGAGGAGGT CAAGGCGTTC ACAGACACCT ATGGCTTCCC CATCATCATC
            K   A   A   F       G   G       G   R   G       M   R   V   V       R   D   Q       A   E   L
 601    AAGGCTGCCT TTGGCGGTGG TGGCCGTGGT ATGCGTGTGG TCCGTGACCA GGCCGAGCTG
            R   D   S   F       E   R   A       T   S   E       A   R   S       A   F   G   N       G   T   V
 661    CGTGACTCGT TCGAGCGAGC CACCTCTGAG GCCCGCTCCG CCTTCGGCAA TGGTACCGTC
            F   V   E   R       F   L   D       K   P   K       H   I   E   V       Q   L   L       G   D   S
 721    TTCGTCGAGC GCTTCCTCGA CAAACCCAAG CACATTGAAG TCCAGCTTCT GGGTGACAGC
            H   G   N   V       V   H   L       F   E   R       D   C   S   V       R   R       H   Q   K
 781    CACGGCAACG TTGTCCATCT GTTTGAGCGT GACTGCTCCG TGCAGCGTCG TCACCAGAAG
            V   V   E   V       A   P   A       K   D   L       P   A   D   V       R   D   R       I   L   A
 841    GTCGTTGAGG TTGCTCCGGC TAAGGACCTG CCAGCCGATG TCCGGGACCG CATCCTGGCC
            D   A   V   K       L   A   K       S   V   N       Y   R   N   A       G   T   A       E   F   L
 901    GATGCTGTGA AGCTGGCCAA GTCCGTCAAC TACCGTAACG CCGGTACAGC TGAGTTCCTG
            V   D   Q   Q       N   R   H       Y   F   I       E   I   N       P   R   I   Q       V   E   H
 961    GTGGACCAGC AGAACCGCCA CTACTTCATT GAAATCAATC CTCGTATCCA AGTCGAGCAC
            T   I   T   E       E   I   T       G   I   D       I   V   A       A   Q   I   Q       I   A   A
1021    ACCATCACCG AAGAGATTAC TGGTATCGAT ATCGTGGCTG CACAGATCCA GATTGCTGCT
            G   A   S   L       E   Q   L       G   L   T       Q   D   R   I       S   A   R       G   F   A
1081    GGTGCAAGCC TCGAGCAACT GGGCCTGACT CAGGACCGCA TCTCCGCCCG CGGATTTGCC
            I   Q   C   R       I   T   T       E   D   P       A   K   G   F       S   P   D       T   G   K
1141    ATTCAATGTC GTATCACCAC GGAAGATCCC GCCAAGGGGT TCTCTCCGGA TACTGGTAAG
            I   E   V   Y       R   S   A       G   G   N       G   V   R   L       D   G   G       N   G   F
1201    ATTGAGGTTT ATCGTTCCGC TGGTGGTAAC GGTGTCCGTC TGGATGGTGG TAACGGTTTC
            A   G   A   I       I   T   P       H   Y   D       S   M   L   V       K   C   T       C   R   G
1261    GCTGGTGCTA TCATCACCCC TCACTACGAC TCCATGCTGG TCAAGTGCAC CTGCCGTGGT
            S   T   Y   E       I   A   R       R   K   V       V   R   A   L       V   E   F       R   I   R
1321    TCGACCTATG AAATCGCTCG TCGCAAGGTT GTGCGTGCCT TGGTCGAGTT CCGTATTCGT
            G   V   K   T       N   I   P       F   L   T       S   L   L   S       H   P   T       F   V   D
1381    GGTGTGAAGA CCAACATTCC CTTCCTGACT TCGCTTCTGA GCCACCCGAC CTTCGTCGAT
            G   N   C   W       T   T   F       I   D   D       T   P   E   L       F   S   L       V   G   S
1441    GGAAACTGCT GGACCACTTT CATCGACGAC ACCCCTGAAT TGTTCTCTCT TGTCGGCAGT
            Q   N   R   A       Q   K   L       L   A   Y       L   G   D   V       A   V   N       G   S   S
1501    CAGAACCGTG CCCAGAAGCT GCTCGCATAC CTCGGCGATG TAGCTGTCAA CGGTAGTAGC
            I   K   G   Q       I   G   E       P   K   L       K   G   D   V       I   K   P       K   L   F
1561    ATCAAGGGCC AAATTGGCGA GCCCAAGCTC AAGGGTGATG TCATCAAGCC GAAGCTTTTC
            D   A   E   G       K   P   L       D   V   S       A   P   C   T       K   G   W       K   Q   T
1621    GATGCCGAGG GCAAGCCGCT TGACGTTTCC GCCCCCTGCA CCAAGGGTTG GAAGCAGATT
            L   D   R   E       G   P   A       A   F   A       K   A   V   R       A   N   K       G   C   L
1681    CTGGACCGGG AGGGTCCGGC TGCCTTTGCG AAGGCCGTGC GTGCCAACAA GGGTTGCTTG
            I   M   D   T       W   R       D   A   H       Q   S   L   L       A   T   R       V   R   T
1741    ATCATGGATA CTACCTGGCG TGACGCCCAC CAGTCTTTGC TGGCCACCCG TGTGCGTACC
            I   D   L   L       N   I   A       H   E   T       S   Y   A   Y       S   N   A       Y   S   L
```

Fig. 9A

```
1801 ATCGACTTGT TGAACATCGC CCATGAGACC AGCTACGCCT ACTCCAATGC GTACAGTTTG
      E  C  W  G  G  A  T  F  D  V  A  M  R  F  L  Y  E  D  P  W
1861 GAATGCTGGG GTGGTGCTAC CTTCGATGTG GCCATGCGTT TCCTCTATGA GGACCCCTGG
      D  R  L  R  K  M  R  K  A  V  P  N  I  P  F  Q  M  L  L  R
1921 GACCGCCTGC GCAAGATGCG TAAGGCTGTT CCTAACATCC CATTCCAGAT GTTGCTCCGT
      G  A  N  G  V  A  Y  S  S  L  P  D  N  A  I  Y  H  F  C  K
1981 GGTGCCAACG GTGTCGCCTA CTCTTCCCTC CCAGACAACG CCATCTACCA CTTCTGTAAG
      Q  A  K  K  C  G  V  D  I  F  R  V  F  D  A  L  N  D  V  D
2041 CAGGCTAAGA AGTGCGGTGT CGACATTTTC CGTGTTTTCG ACGCCCTCAA CGATGTCGAT
      Q  L  E  V  G  I  K  A  V  H  A  A  E  G  V  V  E  A  T  M
2101 CAGCTCGAGG TCGGTATCAA GGCTGTTCAT GCTGCCGAGG TGTTGTCGA GGCCACCATG
      C  Y  S  G  D  M  L  N  P  H  K  K  Y  N  L  E  Y  Y  M  A
2161 TGCTACAGCG GTGACATGCT GAACCCCCAC AAGAAGTACA ACCTGGAGTA CTACATGGCC
      L  V  D  K  I  V  A  M  K  P  H  I  L  G  I  K  D  M  A  G
2221 TTGGTGGATA AGATTGTAGC CATGAAGCCT CACATCCTTG GTATCAAGGA TATGGCCGGT
      V  L  K  P  Q  A  A  R  L  L  V  G  S  I  R  Q  R  Y  P  D
2281 GTGCTGAAGC CCCAGGCCGC TCGCCTGTTG GTGGGCTCCA TCCGTCAGCG CTACCCTGAC
      L  P  I  H  V  H  T  H  D  S  A  G  T  G  V  A  S  M  I  A
2341 CTTCCCATCC ACGTCCACAC CCACGACTCC GCTGGTACTG GTGTAGCTTC CATGATTGCC
      C  A  Q  A  G  A  D  A  V  D  A  A  T  D  S  M  S  G  M  T
2401 TGTGCCCAGG CGGGTGCCGA CGCCGTGGAC GCCGCGACCG ACAGCATGTC CGGTATGACC
      S  Q  P  S  I  G  A  I  L  A  S  L  E  G  T  E  Q  D  P  G
2461 TCCCAGCCTA GCATTGGTGC CATTCTGGCC TCTCTTGAGG GCACTGAGCA AGACCCCGGT
      L  N  L  A  H  V  R  A  I  D  S  Y  W  A  Q  L  R  L  L  Y
2521 CTCAACCTCG CCCACGTGCG CGCTATTGAT AGCTACTGGG CACAGCTGCG CTTGCTCTAC
      S  P  F  E  A  G  L  T  G  P  D  P  E  V  Y  E  H  E  I  P
2581 TCTCCTTTCG AGGCGGGTCT CACTGGCCCC GACCCTGAGG TCTACGAGCA CGAGATCCCT
      G  G  Q  L  T  N  L  I  F  Q  A  S  Q  L  G  L  G  Q  Q  W
2641 GGTGGTCAGT TGACCAACCT TATCTTCCAG GCCAGTCAGC TCGGCTTGGG CCAGCAGTGG
      A  E  T  K  K  A  Y  E  A  A  N  D  L  L  G  D  I  V  K  V
2701 GCCGAAACCA AGAAGGCCTA TGAGGCGGCT AATGATTTAC TCGGCGACAT TGTAAAGGTC
      T  P  T  S  K  V  V  G  D  L  A  Q  F  M  V  S  N  K  L  T
2761 ACTCCCACCT CCAAGGTGGT CGGTGACTTG GCTCAGTTCA TGGTCTCGAA CAAACTGACT
      P  E  D  V  V  E  R  A  G  E  L  D  F  P  G  S  V  L  E  F
2821 CCAGAGGATG TTGTTGAGCG TGCTGGTGAG CTGGACTTCC CTGGTTCTGT GCTCGAATTC
      L  E  G  L  M  G  Q  P  F  G  G  F  P  E  P  L  R  S  R  A
2881 CTCGAAGGTC TCATGGGACA GCCCTTCGGT GGATTCCCCG AGCCATTGCG CTCCCGCGCC
      L  R  D  R  R  K  L  E  K  R  P  G  L  Y  L  E  P  L  D  L
2941 CTGCGCGATC GCCGCAAGCT CGAGAAGCCA CCAGGTCTCT ACCTCGAGCC TTTGGATTTG
      A  K  I  K  S  Q  I  R  E  K  F  G  A  A  T  E  Y  D  V  A
3001 GCTAAGATCA AGAGCCAGAT CCGTGAGAAG TTCGGTGCTG CTACTGAGTA TGACGTGGCC
      S  Y  A  M  Y  P  K  V  F  E  D  Y  K  K  F  V  Q  K  F  G
3061 AGCTATGCCA TGTATCCCAA GGTCTTCGAG GACTACAAGA AGTTCGTCCA GAAGTTCGGT
      D  L  S  V  L  P  T  R  Y  F  L  A  K  P  E  I  G  E  E  F
3121 GATCTCTCCG TCTTGCCCAC ACGGTACTTC TTGGCCAAGC CTGAGATTGG CGAGGAGTTC
      H  V  E  L  E  K  G  K  V  L  I  L  K  L  L  A  I  G  P  L
3181 CACGTTGAGC TGGAGAAGGG TAAGGTGCTC ATCCTGAAGT TGTTGGCCAT CGGCCCTCTT
      S  E  Q  T  G  Q  R  E  V  F  Y  E  V  N  G  E  V  R  Q  V
3241 TCAGAGCAGA CTGGTCAGCG TGAGGTCTTC TACGAAGTCA ACGGTGAGGT GCGCCAGGTC
      A  V  D  D  N  K  A  S  V  D  N  T  S  R  P  K  A  D  V  G
3301 GCTGTTGATG ACAACAAGGC TTCCGTGGAC AACACTTCAC GCCCTAAGGC CGATGTGGGT
      D  S  S  Q  V  G  A  P  M  S  G  V  V  V  E  I  R  V  H  D
3361 GACAGCAGCC AGGTCGGTGC TCCTATGAGC GGTGTGGTTG TTGAAATCCG TGTCCACGAT
      G  L  E  V  K  K  G  D  P  L  A  V  L  S  A  M  K  M
3421 GGTCTGGAGG TTAAGAAGGG TGACCCACTT GCCGTCCTGA GTGCCATGAA GATGGTAAGT
                                                              E  M  ·
3481 TCATTCCGAA TCATTTTTCT CACTGGTCAA CTACAGATGC TAACAGCTTA TCCAGGAAAT
      ·  V  I  S  A  P  H  S  G  K  V  S  S  L  L  V  K  E  G  D  S  ·
3541 GGTTATCTCT GCTCCTCACA GTGAAAGGT CTCCAGCTTG CTGGTCAAGG AGGGCGATTC
      ·  V  D  G  Q  D  L  V  C  K  I  V  K  A       *
3601 TGTGGATGGC CAGGATCTCG TCTGCAAGAT CGTCAAAGCG TAA
```

METHODS FOR C4-DICARBOXYLIC ACID PRODUCTION IN FILAMENTOUS FUNGI

CROSS REFERENCE TO RELATED APPLICATIONS

This application claims priority benefit of U.S. Provisional Application No. 61/357,007, filed Jun. 21, 2010, the entire content of which is incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to methods for improving the production of C4-dicarboxylic acids (e.g., malic acid) in filamentous fungi.

2. Description of the Related Art

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4-dicarboxylic acids can also serve as building block compounds for the production of large volume industrial chemicals, such as 1,4-butanediol, tetrahydrofuran, and gamma-butyrolactone. The cost of producing these large volume industrial chemicals by traditional petrochemical routes has increased significantly due to the high cost of petroleum derived building blocks.

Organic acids are produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids such as fumaric acid and malic acid can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While malic acid is produced commercially today by chemical synthesis from petrochemical feedstocks, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering*, 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974 and WO 2009/155382. Improvement of malic acid production by genetic engineering of *Aspergillus* will enable economical commercial malic acid production by fermentation.

Malic acid overproduction in *Aspergillus* spp. occurs under specific culture conditions (aerobic conditions and high C:N ratio; calcium carbonate is also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra). It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). PCT Application No. PCT/US10/47002, entitled "Methods for Improving Malic Acid Production in Filamentous Fungi" filed Aug. 27, 2010, the content of which is hereby incorporated by reference in its entirety, describes malic acid production in filamentous fungi.

It would be advantageous in the art to improve C4-dicarboxylic acid production, such as malic acid production, in *Aspergillus* as a result of genetic engineering using recombinant DNA techniques. The present invention provides, inter alia, methods for improving C4-dicarboxylic acid production (e.g., malic acid production).

SUMMARY OF THE INVENTION

The present invention relates to methods of producing C4-dicarboxylic acids (e.g., malic acid). In one aspect, the method comprises (a) cultivating a host cell (e.g., a filamentous fungal host cell) comprising a heterologous polynucleotide encoding a C4-dicarboxylic acid transporter described herein; and (b) recovering the C4-dicarboxylic acid (e.g., malic acid). In another aspect, the method comprises (a) transforming into host cell (e.g., a filamentous fungal host cell) a heterologous polynucleotide encoding a C4-dicarboxylic acid transporter described herein; (b) cultivating the transformed organism in a medium; and (c) recovering the C4-dicarboxylic acid (e.g., malic acid). In some aspects of the methods, the host cell further comprises a heterologous polynucleotide encoding a malate dehydrogenase and/or a pyruvate carboxylase.

The present invention also relates to a host cell (e.g., a filamentous fungal host cell, such as *Aspergillus oryzae*) comprising a polynucleotide described herein wherein the host cell secretes and/or is capable of secreting increased levels of a C4-dicarboxylic acid (e.g., malic acid). In some aspects, the host cell further comprises a heterologous polynucleotide encoding a malate dehydrogenase and/or a pyruvate carboxylase.

BRIEF DESCRIPTION OF THE FIGURES

FIG. 4 shows the genomic DNA sequence and the deduced amino acid sequence of an *Aspergillus clavatus* C4-dicarboxylic acid transporter gene (SEQ ID NOs: 1 and 2, respectively).

FIG. 7 shows the genomic DNA sequence and the deduced amino acid sequence of an *Aspergillus fumigates* C4-dicarboxylic acid transporter gene (SEQ ID NOs: 3 and 4, respectively).

FIG. 8 shows the genomic DNA sequence and the deduced amino acid sequence of an *Aspergillus oryzae* NRRL 3488 malate dehydrogenase gene (mdh3) (SEQ ID NOs: 11 and 12, respectively).

FIGS. 9A and 9B together show the genomic DNA sequence and the deduced amino acid sequence of an *Aspergillus oryzae* NRRL 3488 pyruvate carboxylase gene (pyc) (SEQ ID NOs: 13 and 14, respectively).

DEFINITIONS

Figure 1:
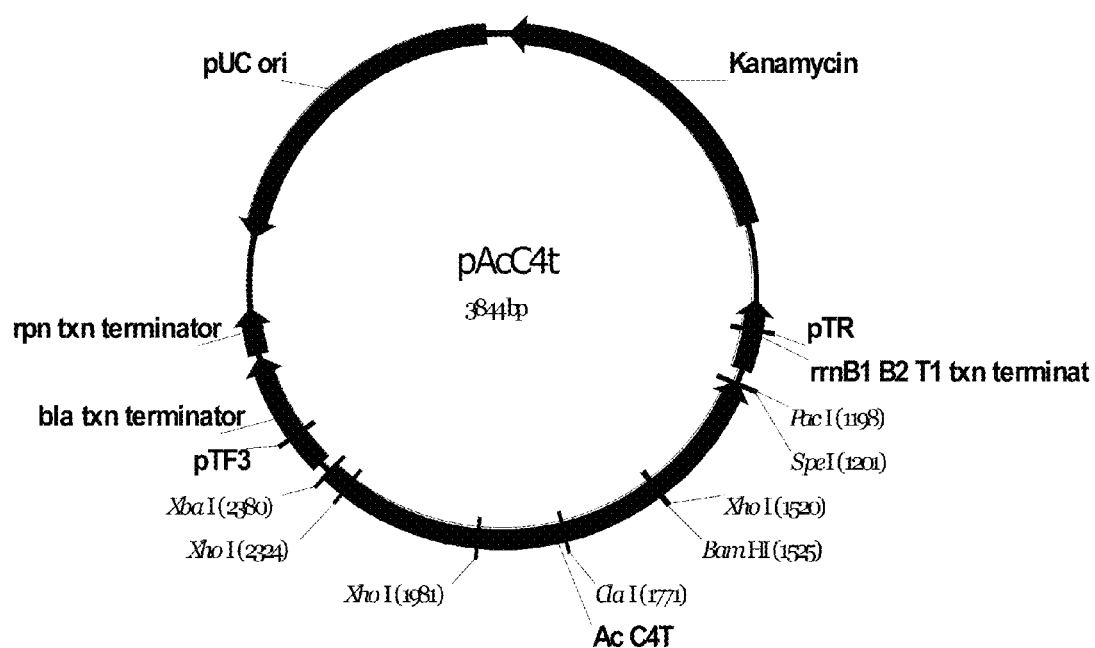
FIG. 1 shows a restriction map of pAcC4T.

C4-dicarboxylic acid transporter: The term "C4-dicarboxylic acid transporter" is defined herein as a dicarboxylic acid permease that can transport malic acid, succinic acid, oxaloacetic acid, malonic acid, and/or fumaric acid outside a cell (Grobler et al., 1995, *Yeast* 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786.

In some aspects, the C4-dicarboxylic acid transporters have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the C4-dicarboxylic acid transporter activity (e.g., malic acid transporter activity) of the mature polypeptide sequence of SEQ ID NO: 2 or the mature polypeptide sequence of SEQ ID NO: 4.

Malate dehydrogenase: The term "malate dehydrogenase" is defined herein as a malate:NAD$^+$ oxidoreductase (EC 1.1.1.37) that catalyzes the reduction of oxaloacetate in the presence of NADH+H$^+$ to malate and NAD$^+$. For purposes of the present invention, malate dehydrogenase activity is determined according to the following procedure. The assay solution consists of 1 mM oxaloacetic acid, 100 mM Tris pH 8.0, 10 mM NaHCO$_3$, 5 mM MgCl$_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malic dehydrogenase (Sigma Chemical Co., St. Louis, Mo., USA) is used as a positive control. One unit of malate dehydrogenase activity equals the amount of enzyme capable of converting 1 µmole of oxaloacetate and NADH+H$^+$ to malate and NAD$^+$ per minute at pH 8.0, 25° C.

In some aspects, the malate dehydrogenases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the malate dehydrogenase activity of the mature polypeptide sequence of SEQ ID NO: 12.

Pyruvate carboxylase: The term "pyruvate carboxylase" is defined herein as a pyruvate:carbon-dioxide ligase (ADP-forming) (EC 6.4.1.1) that catalyzes the carboxylation of pyruvate in the presence of ATP and HCO$_3^-$ to oxaloacetate, ADP, and phosphate. For purposes of the present invention, pyruvate carboxylase activity is determined according to the procedure of the SIGMA® Quality Control Test procedure for pyruvate carboxylase (Sigma Chemical Co., St. Louis, Mo., USA) except the assay uses Tris buffer at pH 8.0. One unit of pyruvate carboxylase activity equals the amount of enzyme capable of converting 1 µmole of pyruvate and CO$_2$ to oxaloacetate per minute at pH 7.8, 30° C.

In some aspects, the pyruvate carboxylases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the pyruvate carboxylase activity of the mature polypeptide sequence of SEQ ID NO: 14.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide whose expression is quantitatively altered by the introduction of one or more (e.g., two, several) extra copies of the polynucleotide into the host cell.

Isolated/purified: The terms "isolated" and "purified" mean a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97%, at least 98% pure, or at least 99% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90%, at least 93% pure, at least 95% pure, at least 97%, at least 98% pure, or at least 99% pure, as determined by agarose electrophoresis.

Coding sequence: The term "coding sequence" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

cDNA sequence: The term "cDNA sequence" means a sequence of DNA following reverse transcription from a mature, spliced, mRNA molecule obtained from a eukaryotic cell. The initial, primary RNA transcript from genomic DNA is a precursor to mRNA that is processed through a series of steps, including splicing, before appearing as mature spliced mRNA. A cDNA sequence lacks intervening intron sequences that may be present in the corresponding genomic DNA sequence. Accordingly, the phrase "the cDNA sequence of SEQ ID NO: X" intends the resulting sequence after the intervening intron sequences of SEQ ID NO: X, if present, are removed. In some instances—when a referenced genomic DNA sequence lacks intervening intron sequences—a cDNA sequence may be identical to its corresponding genomic DNA sequence.

Genomic DNA sequence: The term "genomic DNA sequence" means a DNA sequence found in the genome of a source organism (e.g., a eukaryotic or prokaryotic genome). In some instances, a genomic DNA sequence from a eukaryotic genome contains one or more intervening intron sequences that are removed from the primary RNA transcript as a result of RNA splicing. Accordingly, the phrase "the genomic DNA sequence of SEQ ID NO: Y" intends the corresponding DNA sequence from the source organism which includes intervening intron sequences, if any, that are present before RNA splicing.

Mature polypeptide sequence: The term "mature polypeptide sequence" means the portion of the referenced polypeptide sequence after any post-translational sequence modifications (such as N-terminal processing and/or C-terminal truncation). In some instances, the mature polypeptide sequence may be identical to the entire referenced polypeptide sequence. In one aspect, the mature polypeptide sequence is amino acids 53 to 392 of SEQ ID NO: 2 based on the Vector NIT® program (Invitrogen, CA, USA) that predicts amino acids 1 to 52 of SEQ ID NO: 2 are a signal peptide. In another aspect, the mature polypeptide sequence is amino acids 1 to 393 of SEQ ID NO: 4.

Mature polypeptide coding sequence: The term "mature polypeptide coding sequence" means the portion of the referenced polynucleotide sequence (e.g., genomic or cDNA sequence) that encodes a mature polypeptide sequence. In some instances, the mature polypeptide coding sequence may be identical to the entire referenced polynucleotide sequence. In one aspect, the mature polypeptide coding sequence is nucleotides 157 to 1179 of SEQ ID NO: 1 based on the Vector NIT® program (Invitrogen, CA, USA) that predicts nucleotides 1 to 156 of SEQ ID NO: 1 encode a signal peptide. In another aspect, the mature polypeptide coding sequence is nucleotides 1 to 1182 of SEQ ID NO: 3.

Fragment: The term "fragment" means a polypeptide having one or more (e.g., two, several) amino acids deleted from the amino and/or carboxyl terminus of a referenced polypeptide sequence. In one aspect, the fragment has C4-dicarboxylic acid transporter activity. In another aspect, a fragment contains at least 332 amino acid residues, e.g., at least 352 amino acid residues or at least 372 amino acid residues of SEQ ID NO: 2. In another aspect, a fragment contains at least 332 amino acid residues, e.g., at least 352 amino acid residues or at least 372 amino acid residues of SEQ ID NO: 4.

Subsequence: The term "subsequence" means a polynucleotide having one or more (e.g., two, several) nucleotides deleted from the 5' and/or 3' end of the referenced nucleotide sequence. In one aspect, the subsequence encodes a fragment having C4-dicarboxylic acid transporter activity. In another aspect, a subsequence contains at least 996 nucleotides, e.g., at least 1056 nucleotides or at least 1116 nucleotides of SEQ ID NO: 1. In another aspect, a subsequence contains at least 996 nucleotides, e.g., at least 1056 nucleotides or at least 1116 nucleotides of SEQ ID NO: 3.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Expression: The term "expression" includes any step involved in the production of the polypeptide including, but not limited to, transcription, post-transcriptional modification, translation, post-translational modification, and secretion.

Nucleic acid construct: The term "nucleic acid construct" means a nucleic acid molecule—single-stranded or double-stranded—which is isolated from a naturally occurring gene, modified to contain segments of nucleic acids in a manner that would not otherwise exist in nature, or synthetic, wherein the nucleic acid molecule comprises one or more (e.g., two, several) control sequences.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Host cell: The term "host cell" means any cell type that is susceptible to transformation, transfection, transduction, and the like with a nucleic acid construct or expression vector comprising a polynucleotide of the present invention (e.g., a polynucleotide encoding a C4-dicarboxylic acid transporter). The term "host cell" encompasses any progeny of a parent cell that is not identical to the parent cell due to mutations that occur during replication.

Variant: The term "variant" means a polypeptide having activity, e.g., C4-dicarboxylic acid transporter activity, comprising an alteration, i.e., a substitution, insertion, and/or deletion of one or more (e.g., two, several) amino acid residues at one or more positions. A substitution means a replacement of an amino acid occupying a position with a different amino acid; a deletion means removal of an amino acid occupying a position; and an insertion means adding one or more, e.g., 1-3 amino acids, adjacent to an amino acid occupying a position.

Volumetric productivity: The term "volumetric productivity" refers to the amount of referenced product produced (e.g., the amount of a C4-dicarboxylic acid produced) per volume of the system used (e.g., the total volume of media and contents therein) per unit of time.

Fermentable medium: The term "fermentable medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as a C4-dicarboxylic acid. In some instances, the fermentation medium is derived from a natural source, such as sugar cane, starch, or cellulose, and may be the result of pretreating the source by enzymatic hydrolysis (saccharification).

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention describes the overexpression of specific genes in a host cell, such as a filamentous fungus (e.g., *Aspergillus*) to enhance the production of C4-dicarboxylic acids, (e.g., malic acid) that encompasses transport of the C4-dicarboxylic acid out of the cell via a C4-dicarboxylic acid transporter. In the present invention, the C4-dicarboxylic acid transporter can be any described C4-dicarboxylic acid transporter that is suitable for practicing the present invention. In one aspect, the C4-dicarboxylic acid transporter is a transporter that is overexpressed under culture conditions that produces C4-dicarboxylic acid in high titers. The recombinant host cell may further comprise a heterologous polynucleotide encoding a malate dehydrogenase and/or a heterologous polynucleotide encoding a pyruvate carboxylase.

C4-Dicarboxylic Acid Transporters and Polynucleotides Encoding C4-Dicarboxylic Acid Transporters In one aspect of the recombinant host cells and methods described herein, the C4-dicarboxylic acid transporter is selected from: (a) a C4-dicarboxylic acid transporter having at least 60% sequence identity to SEQ ID NO: 2 or 4, or the mature polypeptide sequence thereof; (b) a C4-dicarboxylic acid transporter encoded by a polynucleotide that hybridizes under low stringency conditions with SEQ ID NO: 1 or 3, the mature polypeptide coding sequence thereof, or the full-length complementary strand of the foregoing; (c) a C4-dicarboxylic acid transporter encoded by a polynucleotide having at least 60% sequence identity to SEQ ID NO: 1 or 3, the mature polypeptide coding sequence thereof, or the full-length complementary strand of the foregoing; (d) a C4-dicarboxylic acid transporter variant comprising a substitution, deletion, and/or insertion of one or more (e.g., two, several) amino acids of SEQ ID NO: 2 or 4, or the mature polypeptide sequence thereof; and (e) a fragment of a polypeptide of (a), (b), (c), or (d) that has C4-dicarboxylic acid transporter activity.

In one aspect, the C4-dicarboxylic acid transporter comprises or consists of an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof. In one aspect, the C4-dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 2 or 4, or the mature polypeptide sequence thereof.

In one aspect, the C4-dicarboxylic acid transporter comprises or consists of an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide sequence thereof. In one aspect, the C4-dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 2 or the mature polypeptide sequence thereof. In another aspect, the C4-dicarboxylic acid transporter comprises an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof. In one aspect, the C4-dicarboxylic acid transporter comprises an amino acid sequence that differs by no more than ten amino acids, e.g., by no more than five amino acids, by no more than four amino acids, by no more than three amino acids, by no more than two amino acids, or by one amino acid from SEQ ID NO: 4 or the mature polypeptide sequence thereof.

In one aspect, the C4-dicarboxylic acid transporter comprises or consists of the amino acid sequence of SEQ ID NO: 2, the mature polypeptide sequence of SEQ ID NO: 2, an allelic variant thereof, or a fragment of the foregoing, having C4-dicarboxylic acid transporter activity. In another aspect, the C4-dicarboxylic acid transporter comprises or consists of the amino acid sequence of SEQ ID NO: 2. In another aspect, the C4-dicarboxylic acid transporter comprises or consists of the mature polypeptide sequence of SEQ ID NO: 2. In another aspect, the C4-dicarboxylic acid transporter comprises or consists of amino acids 1 to 392 of SEQ ID NO: 2.

In one aspect, the C4-dicarboxylic acid transporter comprises or consists of the amino acid sequence of SEQ ID NO: 4, the mature polypeptide sequence of SEQ ID NO: 4, an allelic variant thereof, or a fragment of the foregoing, having C4-dicarboxylic acid transporter activity. In another aspect, the C4-dicarboxylic acid transporter comprises or consists of the amino acid sequence of SEQ ID NO: 4. In another aspect, the C4-dicarboxylic acid transporter comprises or consists of the mature polypeptide sequence of SEQ ID NO: 4. In another aspect, the C4-dicarboxylic acid transporter comprises or consists of amino acids 1 to 393 of SEQ ID NO: 4.

In one aspect, the C4-dicarboxylic acid transporter is encoded by a polynucleotide that hybridizes under at least low stringency conditions, e.g., medium stringency conditions, medium-high stringency conditions, high stringency conditions, or very high stringency conditions with SEQ ID NO: 1 or 3, the mature polypeptide coding sequence thereof, or the full-length complementary strand of the foregoing (see, e.g., J. Sambrook, E. F. Fritsch, and T. Maniatus, 1989, *Molecular Cloning, A Laboratory Manual*, 2d edition, Cold Spring Harbor, N.Y.).

In one aspect, the C4-dicarboxylic acid transporter is encoded by a polynucleotide that hybridizes under at least low stringency conditions, e.g., medium stringency conditions, medium-high stringency conditions, high stringency conditions, or very high stringency conditions with SEQ ID NO: 1, the mature polypeptide coding sequence thereof, or the full-length complementary strand of the foregoing. In another aspect, the C4-dicarboxylic acid transporter is encoded by a polynucleotide that hybridizes under at least low stringency conditions, e.g., medium stringency conditions, medium-high stringency conditions, high stringency conditions, or very high stringency conditions with SEQ ID NO: 3, the mature polypeptide coding sequence thereof, of the full-length complementary strand of the foregoing.

In one aspect, the C4-dicarboxylic acid transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3, the mature polypeptide coding sequence thereof, or the full-length complementary strand of the foregoing.

In one aspect, the C4-dicarboxylic acid transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1, the mature polypeptide coding sequence thereof, or the full-length complementary strand of the foregoing.

In one aspect, the C4-dicarboxylic acid transporter is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 3, the mature polypeptide coding sequence thereof, or the full-length complementary strand of the foregoing.

In one aspect, the C4-dicarboxylic acid transporter is encoded by SEQ ID NO: 1 or 3, or the mature polypeptide coding sequence thereof. In one aspect, the C4-dicarboxylic acid transporter is encoded by SEQ ID NO: 1 or the mature polypeptide coding sequence thereof. In one aspect, the C4-dicarboxylic acid transporter is encoded by SEQ ID NO: 1. In one aspect, the C4-dicarboxylic acid transporter is encoded by SEQ ID NO: 3 or the mature polypeptide coding sequence thereof. In one aspect, the C4-dicarboxylic acid transporter is encoded by SEQ ID NO: 3. In one aspect, the C4-dicarboxylic acid transporter is encoded by a subsequence of SEQ ID NO: 1 or 3, wherein the subsequence encodes a polypeptide having C4-dicarboxylic acid transporter activity. In one aspect, the C4-dicarboxylic acid transporter is encoded by a subsequence of SEQ ID NO: 1, wherein the subsequence encodes a polypeptide having C4-dicarboxylic acid transporter activity. In one aspect, the C4-dicarboxylic acid transporter is encoded by a subsequence of SEQ ID NO: 3, wherein the subsequence encodes a polypeptide having C4-dicarboxylic acid transporter activity.

In one aspect, the C4-dicarboxylic acid transporter is a variant comprising a substitution, deletion, and/or insertion of one or more (e.g., two, several) amino acids of SEQ ID NO: 2 or 4, or the mature polypeptide sequence thereof. In one aspect, the C4-dicarboxylic acid transporter is a variant comprising a substitution, deletion, and/or insertion of one or more amino acids of SEQ ID NO: 2. In one aspect, the C4-dicarboxylic acid transporter is a variant comprising a substitution, deletion, and/or insertion of one or more amino acids of the mature polypeptide sequence of SEQ ID NO: 2. In one aspect, the C4-dicarboxylic acid transporter is a variant comprising a substitution, deletion, and/or insertion of one or more amino acids of SEQ ID NO: 4. In one aspect, the C4-dicarboxylic acid transporter is a variant comprising a substitution, deletion, and/or insertion of one or more amino acids of the mature polypeptide sequence of SEQ ID NO: 4.

Preferably, amino acid changes are of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for activity (e.g., C4-dicarboxylic acid transporter activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the referenced parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of SEQ ID NO: 2 or 4, or the mature polypeptide sequence thereof, is not more than 10, e.g., not more than 1, 2, 3, 4, 5, 6, 7, 8 or 9.

In another aspect, the C4-dicarboxylic acid transporter is a fragment of SEQ ID NO: 2 or 4, or the mature polypeptide sequence thereof, wherein the fragment has C4-dicarboxylic acid transporter activity. In one aspect, the C4-dicarboxylic acid transporter is a fragment of SEQ ID NO: 2 or the mature polypeptide sequence thereof, wherein the fragment has C4-dicarboxylic acid transporter activity. In one aspect, the fragment contains at least 332 amino acid residues, e.g., at least 352 amino acid residues, or at least 372 amino acid residues of SEQ ID NO: 2. In one aspect, the fragment contains a C4-dicarboxylic acid transporter domain, e.g., the putative transporter domain of amino acids 39 to 337 of SEQ ID NO: 2. In another aspect, the C4-dicarboxylic acid transporter is a fragment of SEQ ID NO: 4 or the mature polypeptide sequence thereof, wherein the fragment has C4-dicarboxylic acid transporter activity. In one aspect, the fragment contains at least 332 amino acid residues, e.g., at least 352 amino acid residues, or at least 372 amino acid residues of SEQ ID NO: 4. In one aspect, the fragment contains a C4-dicarboxylic acid transporter domain, e.g., the putative transporter domain of amino acids 41 to 338 of SEQ ID NO: 4.

The C4-dicarboxylic acid transporter may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Techniques used to isolate or clone a polynucleotide—such as a polynucleotide encoding a C4-dicarboxylic acid transporter—as well as any other polypeptide used in any of the aspects mentioned herein, are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shares structural features. See, e.g., Innis et al., 1990, *PCR: A Guide to Methods and Applications*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism, and thus, for example, may be an allelic or species variant of the polypeptide encoding region of the nucleotide sequence.

The polynucleotide of SEQ ID NO: 1 or 3, or a subsequence thereof; as well as the amino acid sequence of SEQ ID NO: 2 or 4; or a fragment thereof; may be used to design nucleic acid probes to identify and clone DNA encoding a C4-dicarboxylic acid transporter from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, e.g., at least 14 nucleotides, at least 25 nucleotides, at least 35 nucleotides, at least 70 nucleotides in lengths. The probes may be longer, e.g., at least 100 nucleotides, at least 200 nucleotides, at least 300 nucleotides, at least 400 nucleotides, at least 500 nucleotides in lengths. Even longer probes may be used, e.g., at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having C4-dicarboxylic acid transporter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or 3, or a subsequence thereof, the carrier material is preferably used in a Southern blot.

For purposes of the present invention, hybridization indicates that the polynucleotide hybridizes to a labeled nucleic acid probe corresponding to SEQ ID NO: 1 or 3, the mature polypeptide coding sequence of SEQ ID NO: 1 or 3, or the full-length complementary strand thereof, or a subsequence of the foregoing; under very low to very high stringency conditions. Molecules to which the nucleic acid probe hybridizes under these conditions can be detected using, for example, X-ray film.

In one aspect, the nucleic acid probe is SEQ ID NO: 1 or 3. In another aspect, the nucleic acid probe is the mature polypeptide coding sequence of SEQ ID NO: 1 or 3. In another aspect, the nucleic acid probe is the mature polypeptide coding sequence of SEQ ID NO: 1. In another aspect, the nucleic acid probe is SEQ ID NO: 1. In another aspect, the nucleic acid probe is the mature polypeptide coding sequence of SEQ ID NO: 3. In another aspect, the nucleic acid probe is SEQ ID NO: 3. In another aspect, the nucleic acid probe is a polynucleotide that encodes the polypeptide of SEQ ID NO: 2 or a fragment thereof. In another aspect, the nucleic acid probe is a polynucleotide that encodes the polypeptide of SEQ ID NO: 4 or a fragment thereof.

For long probes of at least 100 nucleotides in length, very low to very high stringency conditions are defined as prehybridization and hybridization at 42° C. in 5×SSPE, 0.3% SDS, 200 micrograms/mL sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$, using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per mL following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The C4-dicarboxylic acid transporter of the present invention may be obtained from a microorganism of any genus. As used herein, the term "obtained from" in connection with a given source shall mean that the polypeptide encoded by a polynucleotide is produced by the source or by a cell in which the polynucleotide from the source has been inserted.

The C4-dicarboxylic acid transporter may be a bacterial C4-dicarboxylic acid transporter. For example, the C4-dicarboxylic acid transporter may be a Gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* C4-dicarboxylic acid transporter, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* C4-dicarboxylic acid transporter.

In one aspect, the C4-dicarboxylic acid transporter is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* C4-dicarboxylic acid transporter.

In another aspect, the C4-dicarboxylic acid transporter is a *Streptococcus equisimilis, Streptococcus pyogenes, Streptococcus uberis*, or *Streptococcus equi* subsp. *Zooepidemicus* C4-dicarboxylic acid transporter.

In another aspect, the C4-dicarboxylic acid transporter is a *Streptomyces achromogenes, Streptomyces avermitilis, Streptomyces coelicolor, Streptomyces griseus*, or *Streptomyces lividans* C4-dicarboxylic acid transporter.

The C4-dicarboxylic acid transporter may be a fungal C4-dicarboxylic acid transporter. In one aspect, the fungal C4-dicarboxylic acid transporter is a yeast C4-dicarboxylic acid transporter such as a *Candida, Kluyveromyces, Pichia, Saccharomyces, Schizosaccharomyces*, or *Yarrowia* C4-dicarboxylic acid transporter.

In another aspect, the fungal C4-dicarboxylic acid transporter is a filamentous fungal C4-dicarboxylic acid transporter such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* C4-dicarboxylic acid transporter.

In another aspect, the C4-dicarboxylic acid transporter is a *Saccharomyces carlsbergensis, Saccharomyces cerevisiae, Saccharomyces diastaticus, Saccharomyces douglasfi, Saccharomyces kluyveri, Saccharomyces norbensis*, or *Saccharomyces oviformis* C4-dicarboxylic acid transporter.

In another aspect, the C4-dicarboxylic acid transporter is an *Acremonium cellulolyticus, Aspergillus aculeatus, Aspergillus clavatus, Aspergillus awamori, Aspergillus flavus, Aspergillus fumigatus, Aspergillus foetidus, Aspergillus japonicus, Aspergillus nidulans, Aspergillus niger, Aspergillus oryzae, Aspergillus sojae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora*

*crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* C4-dicarboxylic acid transporter.

In one aspect, the C4-dicarboxylic acid transporter is an *Aspergillus* C4-dicarboxylic acid transporter, such as an *Aspergillus clavatus* C4-dicarboxylic acid transporter or an *Aspergillus fumigatus* C4-dicarboxylic acid transporter. In one aspect, the C4-dicarboxylic acid transporter an *Aspergillus clavatus* C4-dicarboxylic acid transporter of SEQ ID NO: 2. In another aspect, the C4-dicarboxylic acid transporter an *Aspergillus fumigatus* C4-dicarboxylic acid transporter of SEQ ID NO: 4.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

The C4-dicarboxylic acid transporter may also be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding a C4-dicarboxylic acid transporter may then be derived by similarly screening a genomic or cDNA library of another microorganism or mixed DNA sample. Once a polynucleotide encoding a C4-dicarboxylic acid transporter has been detected with suitable probe(s) as described herein, the sequence may be isolated or cloned by utilizing techniques that are known to those of ordinary skill in the art (see, e.g., J. Sambrook, E. F. Fritsch, and T. Maniatus, 1989, *Molecular Cloning, A Laboratory Manual,* 2d edition, Cold Spring Harbor, N.Y.).

Malate Dehydrogenases and Polynucleotides Encoding Malate Dehydrogenases

In some aspects of the recombinant host cells and methods of use thereof, the host cells have malate dehydrogenase activity. In some aspects, the host cells comprise a heterologous polynucleotide encoding a malate dehydrogenase. The malate dehydrogenase can be any malate dehydrogenase that is suitable for practicing the invention. In one aspect, the malate dehydrogenase is an enzyme that is present in the cytosol of the host cell.

In one aspect of the recombinant host cells and methods described herein, the malate dehydrogenase is (a) a malate dehydrogenase having at least 60% sequence identity to SEQ ID NO: 12 or the mature polypeptide sequence thereof; (b) a malate dehydrogenase encoded by a polynucleotide that hybridizes under low stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 11 or the mature polypeptide coding sequence thereof, (v) the cDNA sequence of SEQ ID NO: 11 or the mature polypeptide coding sequence thereof; or (vi) the full-length complementary strand of (iv) or (v); (d) a malate dehydrogenase variant comprising a substitution, deletion, and/or insertion of one or more (e.g., two, several) amino acids of SEQ ID NO: 12 or the mature polypeptide sequence thereof; and (e) a fragment of a polypeptide of (a), (b), (c), or (d) that has malate dehydrogenase activity.

In one aspect, the malate dehydrogenase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 12 or the mature polypeptide sequence thereof. In one aspect, the malate dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 12 or the mature polypeptide sequence thereof.

In one aspect, the malate dehydrogenase comprises or consists of the amino acid sequence of SEQ ID NO: 12, the mature polypeptide sequence of SEQ ID NO: 12, an allelic variant thereof, or a fragment of the foregoing, having malate dehydrogenase activity. In another aspect, the malate dehydrogenase comprises or consists of the amino acid sequence of SEQ ID NO: 12. In another aspect, the malate dehydrogenase comprises or consists of the mature polypeptide sequence of SEQ ID NO: 12. In another aspect, the malate dehydrogenase comprises or consists of amino acids 1 to 330 of SEQ ID NO: 12.

In one aspect, the malate dehydrogenase is encoded by a polynucleotide that hybridizes under at least low stringency conditions, e.g., medium stringency conditions, medium-high stringency conditions, high stringency conditions, or very high stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii) (J. Sambrook, E. F. Fritsch, and T. Maniatis, 1989, supra).

In one aspect, the malate dehydrogenase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 11 or the mature polypeptide coding sequence thereof, (v) the cDNA sequence of SEQ ID NO: 11 or the mature polypeptide coding sequence thereof; or (vi) the full-length complementary strand of (iv) or (v).

In one aspect, the malate dehydrogenase is encoded by SEQ ID NO: 11, or the mature polypeptide coding sequence thereof. In one aspect, the malate dehydrogenase is encoded by SEQ ID NO: 11. In one aspect, the malate dehydrogenase is encoded by the mature polypeptide coding sequence of SEQ ID NO: 11. In one aspect, the malate dehydrogenase is encoded by a subsequence of SEQ ID NO: 11, wherein the subsequence encodes a polypeptide having malate dehydrogenase activity. In one aspect, the subsequence contains at least 885 nucleotides, e.g., at least 930 nucleotides or at least 975 nucleotides of SEQ ID NO: 11.

In one aspect, the malate dehydrogenase is a variant comprising a substitution, deletion, and/or insertion of one or more (e.g., two, several) amino acids of SEQ ID NO: 12, or the mature polypeptide sequence thereof, as described supra. In one aspect, the malate dehydrogenase is a variant comprising a substitution, deletion, and/or insertion of one or more amino acids of SEQ ID NO: 12. In one aspect, the malate dehydrogenase is a variant comprising a substitution, deletion, and/or insertion of one or more amino acids of the mature polypeptide sequence of SEQ ID NO: 12. In some aspects, the total number of amino acid substitutions, deletions and/or insertions of the mature polypeptide sequence of SEQ ID NO: 12 or the mature polypeptide sequence thereof is not more than 10, e.g., not more than 1, 2, 3, 4, 5, 6, 7, 8 or 9.

In another aspect, the malate dehydrogenase is a fragment of SEQ ID NO: 12, or the mature polypeptide sequence thereof, wherein the fragment has malate dehydrogenase activity. In one aspect, the fragment contains at least 295 amino acid residues, e.g., at least 310 amino acid residues, or at least 325 amino acid residues of SEQ ID NO: 12.

The malate dehydrogenase may also be an allelic variant or artificial variant of a malate dehydrogenase.

The malate dehydrogenase can also include fused polypeptides or cleavable fusion polypeptides, as described supra.

Techniques used to isolate or clone a polynucleotide encoding a malate dehydrogenase are described supra.

The polynucleotide of SEQ ID NO: 11; or a subsequence thereof; as well as the amino acid sequence of SEQ ID NO: 12; or a fragment thereof; may be used to design nucleic acid probes to identify and clone DNA encoding malate dehydrogenases from strains of different genera or species, as described supra. Such probes are encompassed by the present invention. A genomic DNA or cDNA library prepared from such other organisms may be screened for DNA that hybridizes with the probes described above and encodes a malate dehydrogenase, as described supra.

In one aspect, the nucleic acid probe is SEQ ID NO: 11. In another aspect, the nucleic acid probe is the mature polypeptide coding sequence of SEQ ID NO: 11. In another aspect, the nucleic acid probe is a polynucleotide sequence that encodes SEQ ID NO: 12, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The malate dehydrogenase may be obtained from microorganisms of any genus. In one aspect, the malate dehydrogenase may be a bacterial, a yeast, or a filamentous fungal malate dehydrogenase obtained from the microorganisms described herein. In another aspect, the malate dehydrogenase is an *Aspergillus oryzae* malate dehydrogenase, e.g., the *Aspergillus oryzae* malate dehydrogenase of SEQ ID NO: 12.

Other malate dehydrogenases that can be used to practice the present invention include, but are not limited to, a *Aspergillus nidulans* malate dehydrogenase (AN6717.1; SIMS et al., 2004, *Mycol. Res.* 108: 853-857); *Aspergillus niger* malate dehydrogenase (An16g00120; Pel et al., 2007, *Nature Biotechnology* 25: 221-231); *Phytophthora infestans* malate dehydrogenase (PITG 13614.1; Calcagno et al., 2009, *Mycological Research* 113: 771-781); *Saccharomyces cerevisiae* malate dehydrogenase (YKL085W; McAlister-Henn and Thompson, 1987, *J. Bacteriol.* 169: 5157-5166); *Talaromyces emersonii* malate dehydrogenase (AF439996, AF487682; Maloney et al., 2004, *Eur. J. Biochem.* 271: 3115-3126); and *Ustilago maydis* malate dehydrogenase (um00403, um11161; McCann and Snetselaar, 2008, *Fungal Genetics and Biology* 45: S77-S87), the *Aspergillus oryzae* malate dehydrogenase of SEQ ID NO: 16 (encoded by the polynucleotide sequence of SEQ ID NO: 15; see U.S. application Ser. No. 12/870,523, entitled "Methods for Improving Malic Acid Production in Filamentous Fungi" filed Aug. 27, 2010), or any aspect of the malate dehydrogenase described in the respective reference therein.

The invention embraces any aspect of sequence identity, hybridization, variants and fragments described herein as applied to other malate dehydrogenase polypeptide sequences and polynucleotide sequences described above. For example, in one aspect, the malate dehydrogenase is (a) a malate dehydrogenase having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 16, or the mature polypeptide sequence thereof; (b) a malate dehydrogenase encoded by a polynucleotide that hybridizes under low stringency conditions, e.g., medium stringency conditions, medium-high stringency conditions, high stringency conditions, or very high stringency conditions with (i) SEQ ID NO: 15 or the mature polypeptide coding sequence thereof, (ii) the cDNA sequence of SEQ ID NO: 15 or the mature polypeptide coding sequence thereof, or (iii) the full-length complementary strand of the (i) or (ii); (c) a malate dehydrogenase encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 15 or the mature polypeptide coding sequence thereof, (v) the cDNA sequence of SEQ ID NO: 15 or the mature polypeptide coding sequence thereof, or (vi) the full-length complementary strand of the (iv) or (v); (d) a malate dehydrogenase variant comprising a substitution, deletion, and/or insertion of one or more (e.g., two, several) amino acids of SEQ ID NO: 16 or the mature polypeptide sequence thereof; or (e) a fragment of a polypeptide of (a), (b), (c), or (d) that has malate dehydrogenase activity.

The malate dehydrogenase may also be identified and obtained from other sources including microorganisms isolated from nature (e.g., soil, composts, water, etc.) or DNA samples obtained directly from natural materials (e.g., soil, composts, water, etc.) as described supra.

Pyruvate Carboxylases and Polynucleotides Encoding Pyruvate Carboxylases

In some aspects of the recombinant host cells and methods of use thereof, the host cells have pyruvate carboxylase activity. In some aspects, the host cells comprise a heterologous polynucleotide encoding a pyruvate carboxylase. The pyruvate carboxylase can be any pyruvate carboxylase that is suitable for practicing the invention. In one aspect, the pyruvate carboxylase is an enzyme that is present in the cytosol of the host cell.

In one aspect of the recombinant host cells and methods described herein, the pyruvate carboxylase is (a) a pyruvate carboxylase having at least 60% sequence identity to SEQ ID NO: 14 or the mature polypeptide sequence thereof; (b) a pyruvate carboxylase encoded by a polynucleotide that hybridizes under low stringency conditions with (i) SEQ ID NO: 13 or the mature polypeptide coding sequence thereof, (ii) the cDNA sequence of SEQ ID NO: 13 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 13 or the mature polypeptide coding sequence thereof, (v) the cDNA sequence of SEQ ID NO: 13 or the mature polypeptide coding sequence thereof; or (vi) the full-length complementary strand of (iv) or (v); (d) a pyruvate carboxylase variant comprising a substitution, deletion, and/or insertion of one or more (e.g., two, several) amino acids of SEQ ID NO: 14 or the mature polypeptide sequence thereof; and (e) a fragment of a polypeptide of (a), (b), (c), or (d) that has pyruvate carboxylase activity.

In one aspect, the pyruvate carboxylase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 14, or the mature polypeptide sequence thereof. In one aspect, the pyruvate carboxylase comprises an amino acid sequence that differs by no more than ten amino acids, e.g., by no more than five amino acids, by no more than four amino acids, by no more than three amino acids, by no more than two amino acids, or by one amino acid from SEQ ID NO: 14 or the mature polypeptide sequence thereof.

In one aspect, the pyruvate carboxylase comprises or consists of the amino acid sequence of SEQ ID NO: 14, the mature polypeptide sequence of SEQ ID NO: 14, an allelic variant thereof, or a fragment of the foregoing, having pyruvate carboxylase activity. In another aspect, the pyruvate carboxylase comprises or consists of the amino acid sequence of SEQ ID NO: 14. In another aspect, the pyruvate carboxylase comprises or consists of the mature polypeptide sequence of SEQ ID NO: 14. In another aspect, the pyruvate carboxylase comprises or consists of amino acids 1 to 1193 of SEQ ID NO: 14.

In one aspect, the pyruvate carboxylase is encoded by a polynucleotide that hybridizes under at least low stringency conditions, e.g., medium stringency conditions, medium-high stringency conditions, high stringency conditions, or very high stringency conditions with (i) SEQ ID NO: 13 or the mature polypeptide coding sequence thereof, (ii) the cDNA sequence of SEQ ID NO: 13 or the mature polypeptide coding sequence thereof, or (iii) the full-length complementary strand of (i) or (ii) (J. Sambrook, E. F. Fritsch, and T. Maniatis, 1989, supra).

In one aspect, the pyruvate carboxylase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 13 or the mature polypeptide coding sequence thereof, (v) the cDNA sequence of SEQ ID NO: 13 or the mature polypeptide coding sequence thereof; or (vi) the full-length complementary strand of (iv) or (v).

In one aspect, the pyruvate carboxylase is encoded by SEQ ID NO: 13 or the mature polypeptide coding sequence thereof. In one aspect, the pyruvate carboxylase is encoded by SEQ ID NO: 13. In one aspect, the pyruvate carboxylase is encoded by the mature polypeptide coding sequence of SEQ ID NO: 13. In one aspect, the pyruvate carboxylase is encoded by a subsequence of SEQ ID NO: 13, wherein the subsequence encodes a polypeptide having pyruvate carboxylase activity. In one aspect, the subsequence contains at least 3060 nucleotides, e.g., at least 3240 nucleotides or at least 3420 nucleotides of SEQ ID NO: 13.

In one aspect, the pyruvate carboxylase is a variant comprising a substitution, deletion, and/or insertion of one or more (e.g., two, several) amino acids of SEQ ID NO: 14, or the mature polypeptide sequence thereof, as described supra. In one aspect, the pyruvate carboxylase is a variant comprising a substitution, deletion, and/or insertion of one or more amino acids of SEQ ID NO: 14. In one aspect, the pyruvate carboxylase is a variant comprising a substitution, deletion, and/or insertion of one or more amino acids of the mature polypeptide sequence of SEQ ID NO: 14. In some aspects, the total number of amino acid substitutions, deletions and/or insertions of SEQ ID NO: 14 or the mature polypeptide sequence thereof is not more than 14, e.g., not more than 1, 2, 3, 4, 5, 6, 7, 8 or 9.

In another aspect, the pyruvate carboxylase is a fragment of SEQ ID NO: 14, or the mature polypeptide sequence thereof, wherein the fragment has pyruvate carboxylase activity. In one aspect, the fragment contains at least 1020 amino acid residues, e.g., at least 1080 amino acid residues, or at least 1140 amino acid residues of SEQ ID NO: 14.

The pyruvate carboxylase may also be an allelic variant or artificial variant of a pyruvate carboxylase.

The pyruvate carboxylase can also include fused polypeptides or cleavable fusion polypeptides, as described supra.

The pyruvate carboxylase can also be a variant of a mitochondrial pyruvate carboxylase, such that in vivo importation into the mitochondria is reduced thereby increasing the level of the pyruvate carboxylase variant in the cytosol.

Techniques used to isolate or clone a polynucleotide encoding a pyruvate carboxylase are described supra.

The polynucleotide of SEQ ID NO: 13 or a subsequence thereof, as well as the amino acid sequence of SEQ ID NO: 14 or a fragment thereof, may be used to design nucleic acid probes to identify and clone DNA encoding pyruvate carboxylases from strains of different genera or species, as described supra. Such probes are encompassed by the present invention. A genomic DNA or cDNA library prepared from such other organisms may be screened for DNA that hybridizes with the probes described above and encodes a pyruvate carboxylase, as described supra.

In one aspect, the nucleic acid probe is SEQ ID NO: 13. In another aspect, the nucleic acid probe is the mature polypeptide coding sequence of SEQ ID NO: 13. In another aspect, the nucleic acid probe is a polynucleotide sequence that encodes SEQ ID NO: 14, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The pyruvate carboxylase may be obtained from microorganisms of any genus. In one aspect, the pyruvate carboxylase may be a bacterial, a yeast, or a filamentous fungal pyruvate carboxylase obtained from the microorganisms described herein. In another aspect, the pyruvate carboxylase is an *Aspergillus oryzae* pyruvate carboxylase, e.g., the *Aspergillus oryzae* pyruvate carboxylase of SEQ ID NO: 14.

Other pyruvate carboxylases that can be used to practice the present invention include, but are not limited to, a *Aspergillus clavatus* NRRL 1 pyruvate carboxylase (XP_001271664; Direct Submission, Submitted (26-OCT-2006), The Institute for Genomic Research, 9712 Medical Center Drive, Rockville, Md. 20850, USA); *Aspergillus fumigatus* Af293 pyruvate carboxylase (XP_752054; Nierman et al., 2005, *Nature* 438: 1151-1156); *Aspergillus nidulans* FGSC A4 pyruvate carboxylase (XP_662066; Galagan et al., 2005, *Nature* 438: 1105-1115); *Aspergillus niger* pyruvate carboxylase (An15g02820; Pel et al., 2007, *Nature Biotechnology* 25:

221-231; ASPNG 5061; Panneman et al., Submitted (JUL-1998) to the EMBL/GenBank/DDBJ databases); *Aspergillus terreus* pyruvate carboxylase (093918; Direct Submission, Submitted (OCT-1998) The Institute for Genomic Research, 9712 Medical Center Drive, Rockville, Md. 20850, USA); *Magnaporthe grisea* 70-15 pyruvate carboxylase (XP_367852; Direct Submission, Submitted (26-SEP-2005) Broad Institute of MIT and Harvard, 320 Charles Street, Cambridge, Mass. 02142, USA); *Neurospora crassa* OR74A pyruvate carboxylase (XP_965636; Galagan et al., 2003, *Nature* 422: 859-868); *Rhizopus* oryzaepyruvate carboxylase (RO3G_06931.1); *Saccharomyces cerevisiae* pyruvate carboxylase (NP_009777; Gaffeau et al., 1996, *Science* 274: 546-547); *Schizosaccharomyces pombe* pyruvate carboxylase (NP_595900; Direct Submission, Submitted (29-JUN-2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87). The invention embraces any aspect of sequence identity, hybridization, variants and fragments described herein as applied to the malate dehydrogenase polypeptide sequences and polynucleotide sequences described above.

The pyruvate carboxylase may also be identified and obtained from other sources including microorganisms isolated from nature (e.g., soil, composts, water, etc.) or DNA samples obtained directly from natural materials (e.g., soil, composts, water, etc,) as described supra.

Nucleic Acid Constructs

The present invention also relates to nucleic acid constructs comprising a polynucleotide encoding a C4-dicarboxylic acid transporter (or other polynucleotides described herein, such as a polynucleotide encoding a malate dehydrogenase and/or a pyruvate carboxylase) linked to one or more (e.g., two, several) control sequences that direct the expression of the coding sequence in a suitable host cell under conditions compatible with the control sequences. Such nucleic acid constructs may be used in any of the host cells and methods describe herein. In one aspect, the heterologous polynucleotide encoding a C4-dicarboxylic acid transporter is operably linked to promoter foreign to the polynucleotide. In one aspect, a second heterologous polynucleotide encoding a malate dehydrogenase is operably linked to promoter foreign to the polynucleotide. In one aspect, a third heterologous polynucleotide encoding a pyruvate carboxylase is operably linked to promoter foreign to the polynucleotide.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a C4-dicarboxylic acid transporter or other polynucleotides described herein, such as a polynucleotide encoding a malate dehydrogenase and/or a pyruvate carboxylase). The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant host cells and methods utilizing recombinant expression vectors comprising a polynucleotide encoding a C4-dicarboxylic acid transporter (or other polynucleotides described herein, such as a polynucleotide encoding a malate dehydrogenase and/or a pyruvate carboxylase), a promoter, and transcriptional and translational stop signals. The various nucleotide and control sequences may be joined together to produce a recombinant expression vector that may include one or more (e.g., two, several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

In one aspect, each polynucleotide encoding a C4-dicarboxylic acid transporter, a malate dehydrogenase, and/or a pyruvate carboxylase described herein is contained on an independent vector. In one aspect, two of the polynucleotides are contained on a single vector. In one aspect, all the polynucleotides encoding the C4-dicarboxylic acid transporter, the malate dehydrogenase, and the pyruvate carboxylase are contained on a single vector.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

As described herein, the present invention relates to, inter alia, recombinant host cells comprising a polynucleotide described herein (e.g., a polynucleotide encoding a C4-dicarboxylic acid transporter, a malate dehydrogenase, and/or a pyruvate carboxylase) operably linked to one or more (e.g., two, several) control sequences that direct the production of a polypeptides described herein for the recombinant production of a C4-dicarboxylic acid. The invention also embraces methods of using such host cells for the production of a C4-dicarboxylic acid. The host cell may comprise any one or combination of a plurality of the polynucleotides described. For example, in one aspect, the recombinant host cell comprises a heterologous polynucleotide encoding a C4-dicarboxylic acid transporter; and optionally comprises a heterologous polynucleotide encoding a heterologous polynucleotide encoding a malate dehydrogenase, and/or a heterologous polynucleotide encoding pyruvate decarboxylase; wherein the host cell produces (or is capable of producing) a greater amount of a C4-dicarboxylic acid compared to the host cell without the heterologous polynucleotide encoding the C4-dicarboxylic acid transporter when cultivated under the same conditions.

In one aspect, the recombinant host cell comprises:

(1) a heterologous polynucleotide encoding a C4-dicarboxylic acid transporter, such as a C4-dicarboxylic acid transporter selected from: (a) a C4-dicarboxylic acid transporter having at least 60% sequence identity to SEQ ID NO: 2 or 4, or the mature polypeptide sequence thereof; (b) a C4-dicarboxylic acid transporter encoded by a polynucleotide that hybridizes under low stringency conditions with SEQ ID NO: 1 or 3, the mature polypeptide coding sequence thereof, or the full-length complementary strand of the foregoing; (c) a C4-dicarboxylic acid transporter encoded by a polynucleotide having at least 60% sequence identity to SEQ ID NO: 1 or 3, the mature polypeptide coding sequence thereof, or the full-length complementary strand of the foregoing; (d) a C4-dicarboxylic acid transporter variant comprising a substitution, deletion, and/or insertion of one or more (e.g., two, several) amino acids of SEQ ID NO: 2 or 4, or the mature polypeptide sequence thereof; and (e) a fragment of a polypeptide of (a), (b), (c), or (d) that has C4-dicarboxylic acid transporter activity;

(2) an optional heterologous second polynucleotide encoding a malate dehydrogenase, such as a malate dehydrogenase selected from: (a) a malate dehydrogenase having at least 60% sequence identity to SEQ ID NO: 12 or the mature polypeptide sequence thereof; (b) a malate dehydrogenase encoded by a polynucleotide that hybridizes under low stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 11 or the mature polypeptide coding sequence thereof, (v) the cDNA sequence of SEQ ID NO: 11 or the mature polypeptide coding sequence thereof; or (vi) the full-length complementary strand of (iv) or (v); (d) a malate dehydrogenase variant comprising a substitution, deletion, and/or insertion of one or more (e.g., two, several) amino acids of SEQ ID NO: 12 or the mature polypeptide sequence thereof; and (e) a fragment of a polypeptide of (a), (b), (c), or (d) that has malate dehydrogenase activity; and (3) an optional heterologous third polynucleotide encoding a pyruvate carboxylase, such as a pyruvate carboxylase selected from: (a) a pyruvate carboxylase having at least 60% sequence identity to SEQ ID NO: 14 or the mature polypeptide sequence thereof; (b) a pyruvate carboxylase encoded by a polynucleotide that hybridizes under low stringency conditions with (i) SEQ ID NO: 13 or the mature polypeptide coding sequence thereof, (ii) the cDNA sequence of SEQ ID NO: 13 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 13 or the mature polypeptide coding sequence thereof, (v) the cDNA sequence of SEQ ID NO: 13 or the mature polypeptide coding sequence thereof; or (vi) the full-length complementary strand of (iv) or (v); (d) a pyruvate carboxylase variant comprising a substitution, deletion, and/or insertion of one or more (e.g., two, several) amino acids of SEQ ID NO: 14 or the mature polypeptide sequence thereof; and (e) a fragment of a polypeptide of (a), (b), (c), or (d) that has pyruvate carboxylase activity;

wherein the host cell produces (or is capable of producing) a greater amount of a C4-dicarboxylic acid (e.g., malic acid) compared to the host cell without the one or more polynucleotide(s) (e.g., without the heterologous polynucleotide encoding a C4-dicarboxylic acid transporter), when cultivated under the same conditions.

In one aspect, the host cell comprises a heterologous polynucleotide encoding a C4-dicarboxylic acid transporter described herein (e.g., SEQ ID NO: 1 or 3, or any described aspect thereof) and a heterologous polynucleotide encoding a malate dehydrogenase. In the present invention, the malate dehydrogenase can be any malate dehydrogenase that is suitable for practicing the present invention, as described supra. In another aspect, the host cell comprises a heterologous polynucleotide encoding a C4-dicarboxylic acid transporter described herein (e.g., SEQ ID NO: 1 or 3, or any described aspect thereof) and a heterologous polynucleotide encoding a pyruvate carboxylase. In the present invention, the pyruvate carboxylase can be any pyruvate carboxylase that is suitable for practicing the present invention, as described supra. In particular, the pyruvate carboxylase is preferably an enzyme that is present in the cytosol of the host cell. In one aspect, the host cell comprises a heterologous polynucleotide encoding a C4-dicarboxylic acid transporter described herein (e.g., SEQ ID NO: 1 or 3, or any described aspect thereof), a second heterologous polynucleotide encoding a malate dehydrogenase, and a third heterologous polynucleotide encoding a pyruvate carboxylase.

A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The aspects described below apply to the host cells, per se, as well as methods using the host cells.

The host cell may be any cell capable of the recombinant production of a polypeptide of the present invention, e.g., a prokaryote or a eukaryote, and/or any cell (e.g., any filamentous fungal cell) capable of the recombinant production of a C4-dicarboxylic acid (e.g., malic acid).

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bac-* teriol. 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

In one aspect, the host cell is an *Aspergillus* host cell. In another aspect, the host cell is *Aspergillus oryzae*.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises one or more (e.g., two, several) polynucleotide(s) described herein, wherein the host cell secretes (and/or is capable of secreting) an increased level of C4-dicarboxylic acid compared to the host cell without the one or more polynucleotide(s) when cultivated under the same conditions. In some aspects, the host cell secretes and/or is capable of secreting an increased level of C4-dicarboxylic acid (e.g., malic acid) of at least 5%, e.g., at least 10%, at least 15%, at least 20%, at least 25%, at least 50%, at least 100%, at least 150%, at least 200%, at least 300%, or at 500% compared to the host cell without the one or more polynucleotide(s) (e.g., without the heterologous polynucleotide encoding a C4-dicarboxylic acid transporter), when cultivated under the same conditions.

In any of the aspects of the recombinant host cells and methods described herein, the C4-dicarboxylic acid may be malic acid, succinic acid, oxaloacetic acid, malonic acid, or fumaric acid, or combinations thereof. In some aspects, the C4-dicarboxylic acid is malic acid, succinic acid, or fumaric acid, or combinations thereof. In some aspects, the C4-dicarboxylic acid is malic acid or fumaric acid, or a combination of malic acid and fumaric acid. In some aspects, the C4-dicarboxylic acid is malic acid.

In any of these aspects, the host cell produces (and/or is capable of producing) a C4-dicarboxylic acid at a yield of at least than 10%, e.g., at least than 20%, at least than 30%, at least than 40%, at least than 50%, at least than 60%, at least than 70%, at least than 80%, or at least than 90%, of theoretical.

In any of these aspects, the recombinant host has an C4-dicarboxylic acid volumetric productivity (e.g., malic acid volumetric productivity) greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

The recombinant host cells may be cultivated in a nutrient medium suitable for production of the C4-dicarboxylic acid transporter, malate dehydrogenase, or pyruvate carboxylase using methods well known in the art, as described below.

The C4-dicarboxylic acid transporter, malate dehydrogenase, and pyruvate carboxylase, and activities thereof, can be detected using methods known in the art. These detection methods may include use of specific antibodies, formation of an enzyme product, or disappearance of an enzyme substrate. See, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); and Hanai et al., *Appl. Environ. Microbiol.* 73:7814-7818 (2007)).

Methods

The present invention also relates to methods of using the recombinant host cells described herein for the production of a C4-dicarboxylic acid. In one aspect, the invention embraces a method of producing a C4-dicarboxylic acid (e.g., malic acid), comprising: (a) cultivating any one of the recombinant host cells described herein (e.g., any host cell with C4-dicarboxylic acid transporter activity, and optionally, malate dehydrogenase activity, and/or pyruvate carboxylase activity) in a medium under suitable conditions to produce the C4-dicarboxylic acid; and (b) recovering the C4-dicarboxylic acid. In one aspect, the invention embraces a method of producing a C4-dicarboxylic acid (e.g., malic acid), comprising: (a) cultivating in a medium any one of the recombinant host cells described herein, wherein the host cell comprises a heterologous polynucleotide encoding a C4-dicarboxylic acid transporter; and optionally, a heterologous polynucleotide encoding a malate dehydrogenase, and/or a heterologous polynucleotide encoding a pyruvate decarboxylase under suitable conditions to produce the C4-dicarboxylic acid; and (b) recovering the C4-dicarboxylic acid. In one aspect, the medium is a fermentable medium.

In one aspect of the methods, the C4-dicarboxylic acid (e.g., malic acid) is produced at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

In one aspect of the methods, the amount of produced C4-dicarboxylic acid (e.g., malic acid) is at least 5%, e.g., at least 10%, at least 15%, at least 20%, at least 25%, at least 30%, at least 50%, or at least 100% greater compared to cultivating the host cell without the polynucleotide that encodes the C4-dicarboxylic acid transporter under the same conditions.

In some aspects of the methods, the C4-dicarboxylic acid is selected from malic acid, succinic acid, oxaloacetic acid, malonic acid, and fumaric acid. In one aspect, the C4-dicarboxylic acid is malic acid.

The recombinant C4-dicarboxylic acid can be optionally recovered from the fermentation medium using any procedure known in the art (see, for example, WO 1998/022611 and U.S. Pat. No. 7,601,865) including, but not limited to, chromatography (e.g., size exclusion chromatography, adsorption chromatography, ion exchange chromatography), electrophoretic procedures, differential solubility, osmosis, distillation, extraction (e.g., liquid-liquid extraction), pervaporation, extractive filtration, membrane filtration, membrane separation, reverse, or ultrafiltration. In one example, the C4-dicarboxylic acid is recovered from other material in the fermentation medium by filtration.

In some aspects of the methods, the recombinant C4-dicarboxylic acid before and/or after being optionally purified is substantially pure. With respect to the methods of producing a C4-dicarboxylic acid (or a specific C4-dicarboxylic acid thereof, such as malic acid), "substantially pure" intends a recovered preparation of the C4-dicarboxylic acid that contains no more than 15% impurity, wherein impurity intends compounds other than C4-dicarboxylic acids. In one variation, a preparation of substantially pure C4-dicarboxylic acid is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of C4-dicarboxylic acids for the methods of production and host cells described herein can be performed using methods known in the art. For example, the final C4-dicarboxylic acid product (e.g., malic acid), and other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of C4-dicarboxylic acid in the fermentation broth can also be tested with the culture supernatant. Byproducts and residual sugar in the fermentation medium (e.g., glucose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

The present invention is further described by the following examples that should not be construed as limiting the scope of the invention.

EXAMPLES

Chemicals used as buffers and substrates were commercial products of at least reagent grade.

Strains

*Aspergillus clavatus* NRRL1 and *Aspergillus fumigatus* (*Sartorya fumigata*) Af293 were used as the source C4-dicarboxylic acid transporter genes. *Aspergillus oryzae* NRRL 3488 (or ATCC 56747) was used as a source of a pyruvate carboxylase gene, a malate dehydrogenase gene, and for production of the C4-dicarboxylic acids.

Media

YEG medium was composed of 20 g glucose, 5 g yeast extract, and deionized water to 1 liter.

COVE plates were composed of 1 M sucrose, 2% COVE salt solution, 10 mM acetamide, 15 mM CsCl, and 25 g/l Agar Noble.

COVE salt solution was composed of 26 g KCl, 26 g $MgSO_4.7H_2O$, 76 g $KH_2PO_4$, 50 ml of COVE trace elements solution, and deionized water to 1 liter.

COVE trace elements solution was composed of 0.04 g $Na_2B_4O_7.10H_2O$, 0.04 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$ and deionized water to 1 liter.

Seed medium was composed of 40 g glucose, 6 g Bacto-peptone, 750 mg $KH_2PO_4$, 750 mg $K_2HPO_4$, 100 mg $MgSO_4.7H_2O$, 100 mg $CaCl_2.H_2O$, 5 mg $FeSO_4.7H_2O$, 5 mg NaCl, and deionized water to 1 liter.

Seed medium B is composed of 30 g glucose, 3 g Bacto Peptone, 560 mg $KH_2PO_4$, 560 mg $K_2HPO_4$, 925 mg $NaH_2PO_4.H_2O$, 820 mg $Na_2HPO_4$, 75 mg $MgSO_4.7H_2O$, 75 mg $CaCl_2.H_2O$, 0.75 ml of 1000× Micronutrient Solution, and deionized water to 1 liter.

Acid production medium C is composed of 100 g glucose, 80 g $CaCO_3$, 6 g Bacto Peptone, 150 mg $KH_2PO_4$, 150 mg $K_2HPO_4$, 100 mg $MgSO_4.7H_2O$, 100 mg $CaCl_2.H_2O$, 1 ml 1000× Micronutrient Solution, and deionized water to 1 liter.

1000× Micronutrient Solution is composed of 5 g NaCl, 5 g $FeSO_4.7H_2O$, 1 g citric acid, and deionized water to 1 liter.

PDA plates are composed of 39 g/l potato dextrose agar.

Example 1

Cloning of the *Aspergillus Clavatus* NRRL1 C4-Dicarboxylic Acid Transporter Gene and Construction of Expression Vector pShTh120AcC4T The 1179 bp C4-dicarboxylic acid transporter gene acc4T (ACLA_058030) was synthetically constructed into pAcC4T (FIG. 1; DNA2.0, Menlo Park, Calif., USA). The acc4t gene was amplified from pAcC4T using primers 069735 and 069736 shown below.

```
Primer 069735:
                                     (SEQ ID NO: 5)
5'-GTGTGATAGAACATCGTCCATAATGTTCGAAAATCG-3'

Primer 069736:
                                     (SEQ ID NO: 6)
5'-GTCAGTCACCTCTAGTTAATTAACTAGTCTGCAGCATCCTCATC-3'
```

The PCR reaction mixture was composed of 50 ng pAcC4T template, 200 μM dNTP mixture, 50 μM primer 069735, 50 μM primer 069736, 1× Pol1 reaction buffer (New England Biolabs, MA, USA), and 1 unit Vent Polymerase (New England Biolabs) and deionized water to 50 μl. The PCR reaction was incubated in an EPPENDORF MASTERCYCLER® (Eppendorf Scientific Inc., Westbury, N.Y., USA) programmed for 1 cycle at 94° C. for 3 minutes; 35 cycles at 94° C. for 15 seconds, 59° C. for 30 seconds, and 72° C. for 1 minute; and 1 cycle at 72° C. for 5 minutes. The PCR product was purified by 1% agarose gel electrophoresis in TAE buffer (50 mM Tris base-50 mM acetate-0.1 mM disodium EDTA) and purified using a QIAQUICK® Gel Extraction Kit (QIAGEN Inc., Valencia, Calif., USA).

Figure 2:
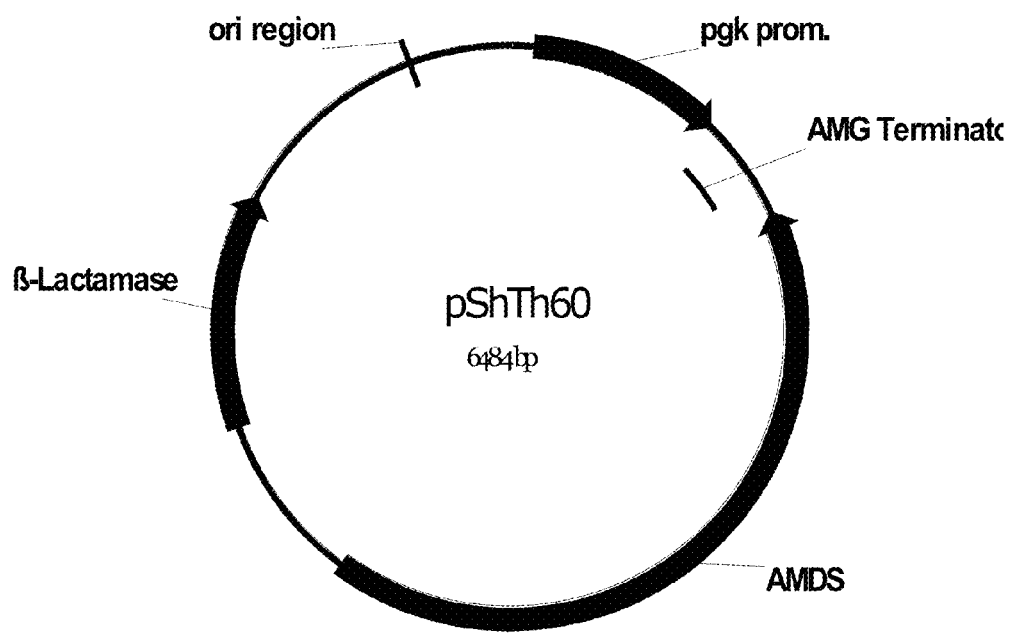
FIG. 2 shows a restriction map of pShTh60.
Figure 3:
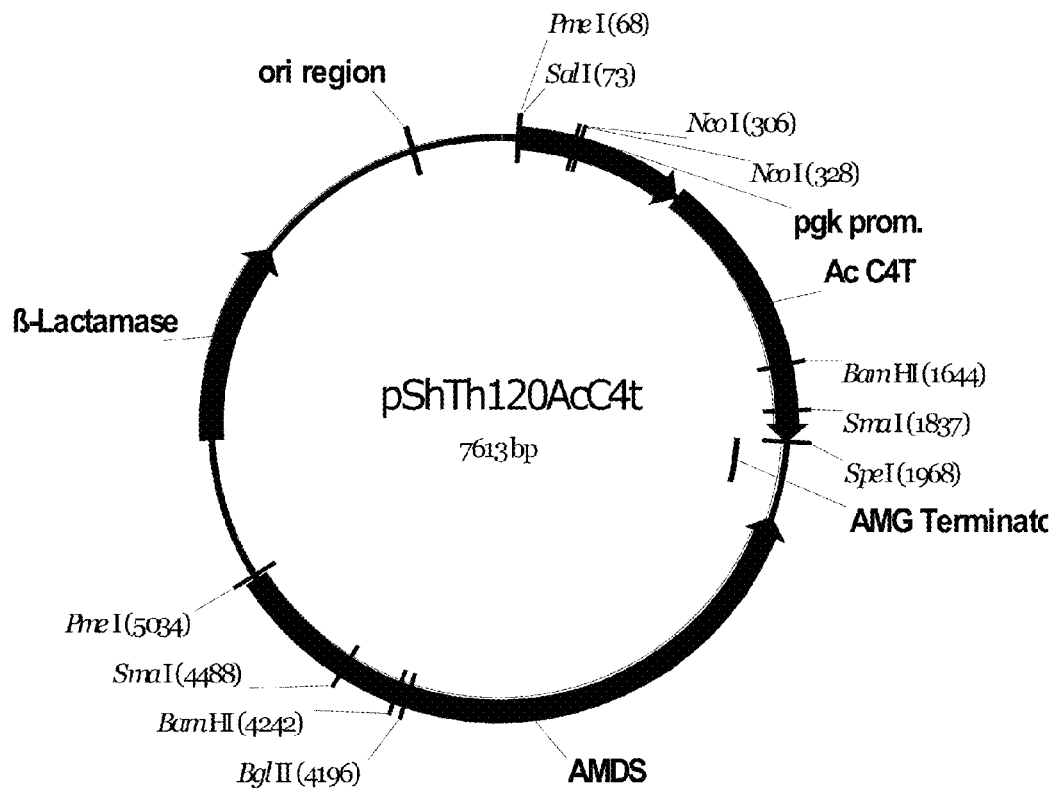
FIG. 3 shows a restriction map of pShTh120AcC4T.

Plasmid pShTh60 (FIG. 2; see also PCT Application No. PCT/US10/47002, entitled "Methods for Improving Malic Acid Production in Filamentous Fungi" filed Aug. 27, 2010) was digested with Sex AI and Pac I then separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit. The purified PCR product above was then inserted into the digested pShTh60 using an In-Fusion™ Cloning Kit (Clontech, Mountain View, Calif., USA) according to the manufacturer's instructions, resulting in pShTh120AcC4T (FIG. 3). Plasmid pShTh120AcC4T was isolated using a QIAfilter Maxi Plasmid Isolation Kit (QIAGEN Inc., Valencia, Calif., USA). DNA sequence analysis was used to confirm the integrity of the acc4t coding sequence using primers 996270 and 065067 shown below using an ABI3130XL DNA Analyzer (Applied Biosystems, Inc., Foster City, Calif., USA) and the primer walking technique with dye-terminator chemistry (Giesecke et al., 1992, *J. Virol. Methods* 38: 47-60).

```
                                     (SEQ ID NO: 7)
Primer 996270: 5'-CTATAGCGAAATGGATTGATTGTCT-3'

(SEQ ID NO: 8)
Primer 065067: 5'-TGACCTTCCACGCTGACCAC-3'
```

The nucleotide sequence (SEQ ID NO: 1) and deduced amino acid sequence (SEQ ID NO: 2) of the *Aspergillus clavatus* acc4t gene are shown in FIG. 4. The genomic coding sequence of 1179 bp (including stop codon) encodes a polypeptide of 392 amino acids with a predicted mass of 43.4 kDa and an isoelectric pH of 7.85. The gene contains no introns. Using the Vector NTI® program (Invitrogen, CA, USA), a signal peptide of 52 residues was predicted, resulting in a predicted mature protein containing 340 amino acids.

Example 2

Figure 5:
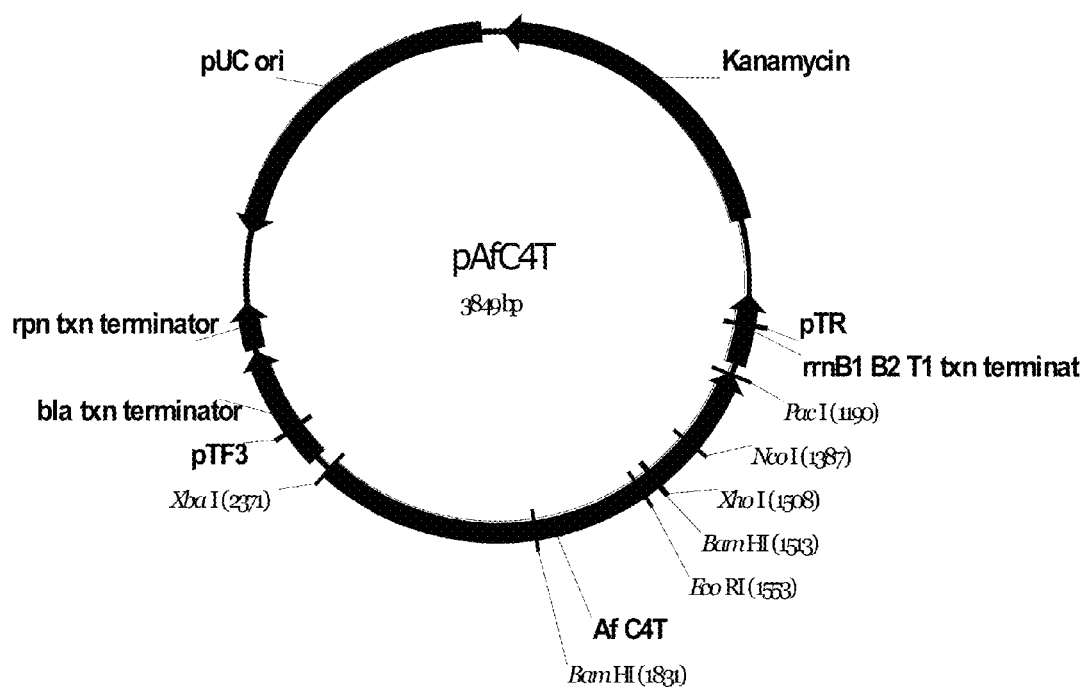
FIG. 5 shows a restriction map of pAfC4T.

Cloning of the *Aspergillus* Fumigates Af293 C4-Dicarboxylic Acid Transporter Gene and Construction of Expression Vector pShTh121AfC4T The 1182 bp C4-dicarboxylic acid transporter gene sequence afc4t (AFUA_8G04630) was synthetically constructed into pAfC4T (FIG. 5; DNA2.0). The afc4t gene was amplified from pAfC4T using primers 069737 and 069738 shown below.

```
Primer 069737:
                                     (SEQ ID NO: 9)
5-GTGTGATAGAACATCGTCCATAATGTTCAACGATCATGATCA-3'

Primer 069738:
                                     (SEQ ID NO: 10)
5'-GTCAGTCACCTCTAGTTAATTAATTAATCTAGCACATCCTCGTC-3'
```

The PCR reaction mixture was composed of 50 ng pAtC4T template, 200 μM dNTP mixture, 50 μM primer 069737, 50 μM primer 069738, 1× Pol1 reaction buffer, 1 unit Vent Polymerase and deionized water to 50 μl. The PCR reaction was incubated in an EPPENDORF MASTERCYCLER® programmed for 1 cycle at 94° C. for 3 minutes; 35 cycles at 94° C. for 15 seconds, 59° C. for 30 seconds, and 72° C. for 1 minute; and 1 cycle at 72° C. for 5 minutes. The PCR product was purified by 1% agarose gel electrophoresis in TAE buffer (50 mM Tris base-50 mM acetate-0.1 mM disodium EDTA) and purified using a QIAQUICK® Gel Extraction Kit.

Figure 6:
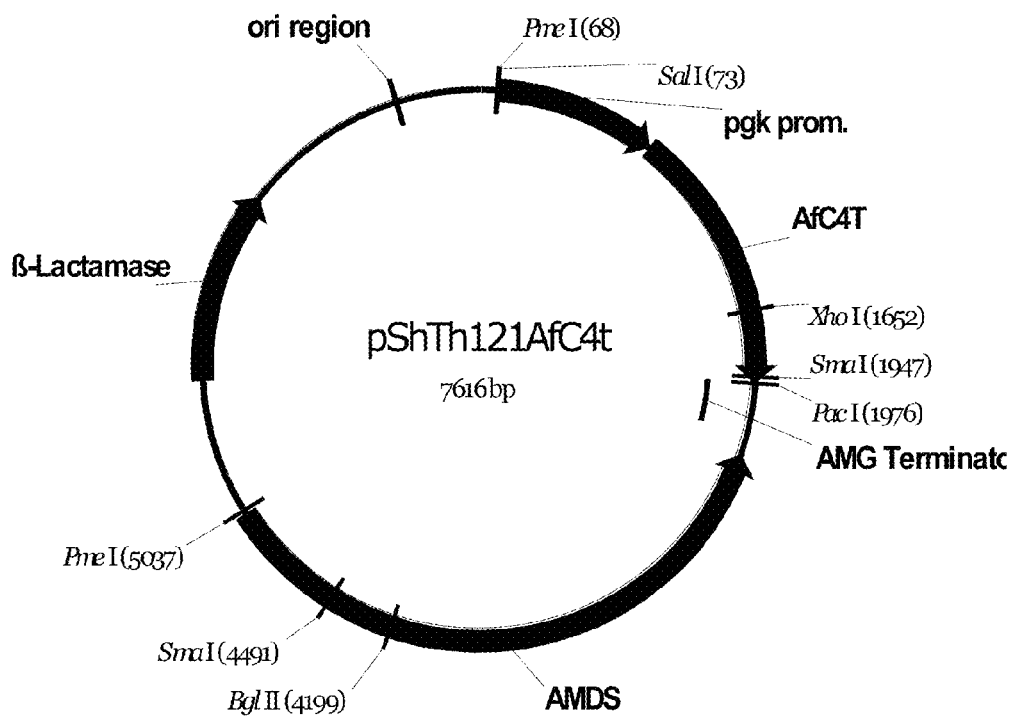
FIG. 6 shows a restriction map of pShTh121AfC4T.

Plasmid pShTh60 (FIG. 2) was digested and purified as described above. The purified PCR product above was then inserted into the digested pShTh60 using an InFusion Cloning Kit according to the manufacturer's instructions resulting in plasmid pShTh121AfC4T (FIG. 6). Plasmid pShTh121AfC4T was isolated using a QIAfilter Maxi Plasmid Isolation Kit. DNA sequence analysis was used to confirm the integrity of the afc4t coding sequence using primers 996270 and 065067 as described above.

The nucleotide sequence (SEQ ID NO: 3) and deduced amino acid sequence (SEQ ID NO: 4) of the *Aspergillus fumigates* afc4t gene are shown in FIG. 7. The genomic coding sequence of 1182 bp (including stop codon) encodes a polypeptide of 393 amino acids with a predicted mass of 43.8 kDa and an isoelectric pH of 7.30. The gene contains no introns.

Example 3

Transformation of Expression Vector Fragments of pShTh120AcC4T and pShTh121AfC4T into *Aspergillus Oryzae* NRRL3488 (ShTh1200 and ShTh1210)

Protoplast preparation and transformation of *Aspergillus oryzae* NRRL3488 were performed by inoculating approximately $2 \times 10^7$ spores into 100 ml YEG medium and incubating the flask at 27° C. for 16-18 hours at 140 rpm. Mycelia were collected by pouring the culture through a sterile funnel lined with MIRACLOTH® (Calbiochem, San Diego, Calif., USA) and rinsing with 50 ml of 0.7 M KCl. The washed mycelia were resuspended in a 125 ml flask with 20 ml of protoplasting solution composed of 5 mg of GLUCANEX™ (Novozymes NS, Bagsvrd, Denmark) and 0.5 mg of chitinase (Sigma Chemical Co., St. Louis, Mo., USA) per ml of 0.7 M KCl (filter sterilized) and incubated at 34° C., for 30 minutes with mixing at 80 rpm. The protoplasting solution was poured through a sterile funnel lined with MIRACLOTH® and rinsed with 50 ml of STC buffer (1 M sorbitol-10 mM Tris-HCl pH 6.5-10 mM $CaCl_2$). The flow-through was collected in two 50 ml polypropylene tubes. The tubes were spun in the centrifuge at 1300×g for 10 minutes at room temperature. The supernatant was discarded and the protoplast pellet was resuspended in 20 ml of STC buffer. The protoplasts were washed by two rounds of resuspending the pellet in 20 ml of STC and centrifugation at 1300×g for 10 minutes at room temperature. The final pellet was resuspended in 2 ml of STC. The protoplasts were counted by removing a 10 µl sample and counting them in a haemocytometer (VWR, West Chester, Pa., USA). The volume was adjusted with STC to obtain a protoplast concentration of $2 \times 10^7$ per ml.

The plasmid vectors were prepared for transformation by restriction digestion with Pme I. The approximately 5 kb expression cassette from each construct was separated from the vector sequences by 0.8% agarose gel electrophoresis in TBE buffer and purified using a QIAQUICK® Gel Extraction Kit.

Four transformation reactions were prepared for each expression vector. For each reaction, a 100 µl solution of protoplast preparation was transferred to a 12 ml polypropylene tube, to which was added 2-5 µg of restriction digested plasmid vector above and 250 µl of polyethylene glycol solution (60% w/v polyethylene glycol (PEG), 10 mM Tris 6.5, 10 mM CaCl), followed by gentle mixing and incubation at 37° C. for 30 minutes. Each transformation reaction was diluted with 6 ml STC, followed by three separate aliquots onto COVE plates. Each plate was then incubated at 34° C. for 7-10 days. The resulting transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C. Transformants containing the expression vector fragment of pShTh120AcC4T were designated ShTh1200. Transformants containing the expression vector fragment of pShTh121AfC4T were designated ShTh1210.

Example 4

Production of Malic Acid in Shake Flask Cultures of *Aspergillus Oryzae* Transformants Containing Expression Vector Fragments of pShTh120AcC4T and pShTh121AfC4T (ShTh1200 and ShTh1210)

Spores from transformants ShTh1200 and ShTh1210 described above and *Aspergillus oryzae* NRRL 3488 as a control were plated onto individual COVE plates and allowed to sporulate at 34° C. for 5 to 7 days. Spores were collected in 0.1% TWEEN® 80 and counted using a hemacytometer. Seed cultures were prepared in 250 ml flasks containing 100 ml of seed medium B and inoculated with $2 \times 10^8$ total spores. Seed cultures were grown for approximately 17 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 2-10 days.

Quantitation of malic acid for the shake flask culture transformants was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5µ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:10 in HPLC Running Buffer composed of 850 ml of 64 mM phosphate buffer and 150 ml of methanol pH 1.65. The samples were then filtered through a 25 mm 0.45 micron polyethersulfone membrane (Whatman, Florham Park, N.J., USA) and 1.5 ml of the filtrates were placed into a HPLC vial for acid analysis. The remaining amount of the shake flask cultures were filtered through 3 layers of cheese cloth and rinsed three times with 10 volumes of double distilled sterile water to remove insoluble $CaCO_3$. Cell pellets were harvested from the cheese cloth, placed into a 15 ml culture tube and stored at −20° C.

RP-HPLC was performed using an injection volume of 10 µl at a flow rate of 0.7 ml/minute (isocratic) with a column temperature of 25° C. and run time of 11 minutes. Detection was set at 210 nm, 8 nm bandwidth, with the reference at 360 nm, 40 nm bandwidth. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was 5%. Malic acid shows $R^2 \geq 0.9999$.

*Aspergillus oryzae* transformants containing pShTh120AcC4T (strains ShTh1200) showed an improvement in malic acid production over the *Aspergillus oryzae* NRRL 3488 control strains and comparable malic acid production to *Aspergillus oryzae* ShTh1040 strains (see PCT Application No. PCT/US10/47002, filed Aug. 27, 2010). *Aspergillus oryzae* transformants containing pShTh121AfC4T (strains ShTh1210) showed a slight improvement in malic acid production over the *Aspergillus oryzae* NRRL 3488 control strains and lower malic acid production compared to *Aspergillus oryzae* ShTh1040 strains.

Example 5

Fermentation of *Aspergillus Oryzae* Transformants Containing Expression Vector Fragments of pShTh120AcC4T (ShTh1200)

*Aspergillus oryzae* transformants above and control transformant *Aspergillus oryzae* ShTh1040 (see PCT Application No. PCT/US10/47002, filed Aug. 27, 2010) were grown for approximately 7 days at 32° C. on PDA plates. A 5-6 ml volume of sterile 50 mM sodium phosphate buffer (pH 6.8) containing 0.1% TWEEN® 80 was added to each plate and spores were suspended by scraping with an inoculating loop. Each suspension was transferred by pipette to a 50 ml conical tube. For each tube, 25 ml of sterile sodium phosphate buffer was added to a 500 ml unbaffled flask containing 75 ml of seed medium, which was then inoculated with 2 ml of spore suspension. The flasks were then incubated at 32° C. and 180 rpm for about 24 hours. The seed flasks are combined to supply the 144 ml inoculum required per tank.

Three-liter fermentors containing 1.8 liters of medium were individually inoculated by introducing 144 ml (8%) of the seed culture broth from the combined seed flasks of either an *Aspergillus oryzae* pShTh120AcC4T transformant or an *Aspergillus oryzae* ShTh1040 transformant. The fermentors were equilibrated at 32±0.1° C. and stirred at 500 rpm. Inlet air flow was maintained at 1 v/v/m. Samples were withdrawn daily and analyzed for malic acid production, and the fermentations were completed after approximately 7 days.

Quantitation of malic acid in the fermentations was performed as described in Example 4. The relative malic acid titer of *Aspergillus oryzae* pShTh120AcC4T (ShTh1200) transformants were comparable to the *Aspergillus oryzae* ShTh1040 transformants, indicating that the *Aspergillus oryzae* pShTh120AcC4T transformants outperform the *Aspergillus oryzae* NRRL 3488 control (which lack the overexpressed C4-dicarboxylic acid transporter gene) based on ShTh1040 and NRRL 3488 comparisons previously described.

The present invention may be further described by the following numbered paragraphs:

[1] A method of producing a C4-dicarboxylic acid, comprising:
  (a) cultivating a host cell comprising a heterologous polynucleotide encoding a C4-dicarboxylic acid transporter; wherein the transporter is selected from:
    (i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof;
    (ii) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing;
    (iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3, the mature polypeptide coding sequence thereof;
    (iv) a C4-dicarboxylic acid transporter variant comprising a substitution, deletion, and/or insertion of one or more (e.g., two, several) amino acids of SEQ ID NO: 2 or 4, or the mature polypeptide sequence thereof; and
    (v) a fragment of a C4-dicarboxylic acid transporter of (i), (ii), (iii), or (iv) that has C4-dicarboxylic acid transporter activity; and
  (b) recovering the C4-dicarboxylic acid.

[2] A method of producing a dicarboxylic acid, comprising:
  (a) cultivating a host cell comprising a heterologous polynucleotide encoding a C4-dicarboxylic acid transporter; wherein the transporter is selected from:
    (i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide sequence thereof;
    (ii) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 1, the mature polypeptide coding sequence thereof, or the full-length complementary strand of the foregoing;
    (iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or the mature polypeptide coding sequence thereof;
    (iv) a C4-dicarboxylic acid transporter variant comprising a substitution, deletion, and/or insertion of one or more (e.g., two, several) amino acids of SEQ ID NO: 2 or the mature polypeptide sequence thereof; and
    (v) a fragment of a C4-dicarboxylic acid transporter of (i), (ii), (iii), or (iv) that has C4-dicarboxylic acid transporter activity; and
  (b) recovering the C4-dicarboxylic acid.

[3] A method of producing a C4-dicarboxylic acid, comprising:
  (a) cultivating a host cell comprising a heterologous polynucleotide encoding a C4-dicarboxylic acid transporter; wherein the transporter is selected from:
    (i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof;
    (ii) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 3, the mature polypeptide coding sequence thereof, or the full-length complementary strand of the foregoing;

(iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the mature polypeptide coding sequence thereof;

(iv) a C4-dicarboxylic acid transporter variant comprising a substitution, deletion, and/or insertion of one or more (e.g., two, several) amino acids of SEQ ID NO: 4 or the mature polypeptide sequence thereof; and (v) a fragment of a C4-dicarboxylic acid transporter of (i), (ii), (iii), or (iv) that has C4-dicarboxylic acid transporter activity; and (b) recovering the C4-dicarboxylic acid.

[4] The method of any one of paragraphs [1]-[3], wherein the C4-dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 or 4, or the mature polypeptide sequence thereof.

[5] The method of any one of paragraphs [1]-[4], wherein the C4-dicarboxylic acid transporter is encoded by a polynucleotide that hybridizes under low stringency conditions, low-medium stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing.

[6] The method of any one of paragraphs [1]-[5], wherein the C4-dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1 or 3, or the mature polypeptide coding sequence thereof.

[7] The method of any one of paragraphs [1]-[6], wherein the C4-dicarboxylic acid transporter comprises or consists of SEQ ID NO: 2 or 4.

[8] The method of any one of paragraphs [1]-[6], wherein the C4-dicarboxylic acid transporter comprises or consists of the mature polypeptide sequence of SEQ ID NO: 2 or 4.

[9] The method of paragraph [8], wherein the mature polypeptide sequence of SEQ ID NO: 2 is amino acids 53 to 392 of SEQ ID NO: 2.

[10] The method of paragraph [8] or [9], wherein the mature polypeptide sequence of SEQ ID NO: 4 is amino acids 1 to 393 of SEQ ID NO: 4.

[11] The method of any one of paragraphs [1]-[6], wherein the C4-dicarboxylic acid transporter is a fragment of SEQ ID NO: 2 or 4, wherein the fragment has C4-dicarboxylic acid transporter activity.

[12] The method of any one of paragraphs [1]-[6], wherein the C4-dicarboxylic acid transporter is a variant comprising a substitution, deletion, and/or insertion of one or more (e.g., two, several) amino acids of SEQ ID NO: 2 or 4, or the mature polypeptide sequence thereof.

[13] The method of any one of paragraphs [1]-[12], wherein the heterologous polynucleotide encoding the C4-dicarboxylic acid transporter is operably linked to a promoter foreign to the polynucleotide.

[14] The method of any one of paragraphs [1]-[13], wherein the host cell further comprises a heterologous second polynucleotide encoding a malate dehydrogenase (e.g., the malate dehydrogenase of SEQ ID NO: 11, or any described aspect thereof).

[15] The method of paragraph [14], wherein the heterologous second polynucleotide encoding a malate dehydrogenase is operably linked to a promoter foreign to the polynucleotide.

[16] The method of any one of paragraphs [1]-[15], wherein the host cell further comprises a heterologous third polynucleotide encoding a pyruvate carboxylase (e.g., the pyruvate carboxylase of SEQ ID NO: 13, or any described aspect thereof).

[17] The method of paragraph [16], wherein the heterologous third polynucleotide encoding a pyruvate carboxylase is operably linked to a promoter foreign to the polynucleotide.

[18] The method of any one of paragraphs [1]-[17], wherein the host cell is a filamentous fungal host cell.

[19] The method of paragraph [18], wherein the filamentous fungal host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma* cell.

[20] The method of paragraph [19], wherein the host cell is an *Aspergillus* host cell.

[21] The method of paragraph [20], wherein the *Aspergillus* host cell is an *Aspergillus oryzae* host cell.

[22] The method of any one of paragraphs [1]-[21], wherein the level of the C4-dicarboxylic acid is increased by at least 25%, e.g., at least 50%, at least 100%, at least 150%, at least 200%, at least 300%, or at 500% compared to the host cell without the polynucleotide encoding the heterologous polynucleotide when cultivated under the same conditions.

[23] The method of any one of paragraphs [1]-[22], wherein the C4-dicarboxylic acid is selected from malic acid, succinic acid, oxaloacetic acid, malonic acid, and fumaric acid.

[24] The method of paragraph [23], wherein the C4-dicarboxylic acid is malic acid.

[25] A method for increasing C4-dicarboxylic acid production, comprising:

(a) transforming into a host cell a heterologous polynucleotide encoding a C4-dicarboxylic acid transporter; wherein the transporter is selected from:

(i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof;

(ii) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing;

(iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3, the mature polypeptide coding sequence thereof;

(iv) a C4-dicarboxylic acid transporter variant comprising a substitution, deletion, and/or insertion of one or more (e.g., two, several) amino acids of SEQ ID NO: 2 or 4, or the mature polypeptide sequence thereof; and (v) a fragment of a C4-dicarboxylic acid transporter of (i), (ii), (iii), or (iv) that has C4-dicarboxylic acid transporter activity; and (b) cultivating the transformed host cell in a medium; and (c) recovering the C4-dicarboxylic acid.

[26] A method for increasing C4-dicarboxylic acid production, comprising:

(a) transforming into a host cell a heterologous polynucleotide encoding a C4-dicarboxylic acid transporter; wherein the transporter is selected from:

(i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide sequence of SEQ ID NO: 2;

(ii) a C4-dicarboxylic acid transporter encoded by a polynucleotide that hybridizes under low stringency conditions, medium stringency conditions, medium-high stringency conditions, high stringency conditions, or very high stringency conditions with the mature polypeptide coding sequence of SEQ ID NO: 1, or the full-length complementary strand thereof;

(iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;

(iv) a C4-dicarboxylic acid transporter variant comprising a substitution, deletion, and/or insertion of one or more (e.g., two, several) amino acids of the mature polypeptide sequence of SEQ ID NO: 2; and (v) a fragment of a C4-dicarboxylic acid transporter of (i), (ii), (iii), or (iv) that has C4-dicarboxylic acid transporter activity; and (b) cultivating the transformed host cell in a medium; and (c) recovering the C4-dicarboxylic acid.

[27] A method for increasing C4-dicarboxylic acid production, comprising:

(a) transforming into a host cell a heterologous polynucleotide encoding a C4-dicarboxylic acid transporter; wherein the transporter is selected from:

(i) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof;

(ii) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 3, the mature polypeptide coding sequence thereof, or the full-length complementary strand of the foregoing;

(iii) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the mature polypeptide coding sequence thereof;

(iv) a C4-dicarboxylic acid transporter variant comprising a substitution, deletion, and/or insertion of one or more (e.g., two, several) amino acids of SEQ ID NO: 4 or the mature polypeptide sequence thereof; and (v) a fragment of a C4-dicarboxylic acid transporter of (i), (ii), (iii), or (iv) that has C4-dicarboxylic acid transporter activity; and (b) cultivating the transformed host cell in a medium; and (c) recovering the C4-dicarboxylic acid.

[28] The method of any one of paragraphs [25]-[27], wherein the C4-dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 or 4, or the mature polypeptide sequence thereof.

[29] The method of any one of paragraphs [25]-[28], wherein the C4-dicarboxylic acid transporter is encoded by a polynucleotide that hybridizes under low stringency conditions, low-medium stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing.

[30] The method of any one of paragraphs [25]-[29], wherein the C4-dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1 or 3, or the mature polypeptide coding sequence thereof.

[31] The method of any one of paragraphs [25]-[30], wherein the C4-dicarboxylic acid transporter comprises or consists of SEQ ID NO: 2 or 4.

[32] The method of any one of paragraphs [25]-[30], wherein the C4-dicarboxylic acid transporter comprises or consists of the mature polypeptide sequence of SEQ ID NO: 2 or 4.

[33] The method of paragraph [32], wherein the mature polypeptide sequence of SEQ ID NO: 2 is amino acids 53 to 392 of SEQ ID NO: 2.

[34] The method of paragraph [32] or [33], wherein the mature polypeptide sequence of SEQ ID NO: 4 is amino acids 1 to 393 of SEQ ID NO: 4.

[35] The method of any one of paragraphs [25]-[30], wherein the C4-dicarboxylic acid transporter is a fragment of SEQ ID NO: 2 or 4, wherein the fragment has C4-dicarboxylic acid transporter activity.

[36] The method of any one of paragraphs [25]-[30], wherein the C4-dicarboxylic acid transporter is a variant comprising a substitution, deletion, and/or insertion of one or more (e.g., two, several) amino acids of SEQ ID NO: 2 or 4, or the mature polypeptide sequence thereof.

[37] The method of any one of paragraphs [25]-[36], wherein the heterologous polynucleotide encoding the C4-dicarboxylic acid transporter is operably linked to a promoter foreign to the polynucleotide.
[38] The method of any one of paragraphs [25]-[37], wherein the host cell further comprises a heterologous second polynucleotide encoding a malate dehydrogenase (e.g., the malate dehydrogenase of SEQ ID NO: 11, or any described aspect thereof).
[39] The method of paragraph [38], wherein the heterologous second polynucleotide encoding a malate dehydrogenase is operably linked to a promoter foreign to the polynucleotide.
[40] The method of any one of paragraphs [25]-[39], wherein the host cell further comprises a heterologous third polynucleotide encoding a pyruvate carboxylase (e.g., the pyruvate carboxylase of SEQ ID NO: 13, or any described aspect thereof).
[41] The method of paragraph [40], wherein the heterologous third polynucleotide encoding a pyruvate carboxylase is operably linked to a promoter foreign to the polynucleotide.
[42] The method of any one of paragraphs [25]-[41], wherein the host cell is a filamentous fungal host cell.
[43] The method of paragraph [42], wherein the filamentous fungal host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma* cell.
[44] The method of paragraph [43], wherein the host cell is an *Aspergillus* host cell.
[45] The method of paragraph [44], wherein the *Aspergillus* host cell is an *Aspergillus oryzae* host cell.
[46] The method of any one of paragraphs [25]-[45], wherein the level of the C4-dicarboxylic acid is increased by at least 25%, e.g., at least 50%, at least 100%, at least 150%, at least 200%, at least 300%, or at 500% compared to the host cell without the polynucleotide encoding the heterologous polynucleotide when cultivated under the same conditions.
[47] The method of any one of paragraphs [25]-[46], wherein the C4-dicarboxylic acid is selected from malic acid, succinic acid, oxaloacetic acid, malonic acid, and fumaric acid.
[48] The method of paragraph [47], wherein the C4-dicarboxylic acid is malic acid.
[49] A host cell comprising a heterologous polynucleotide encoding a C4-dicarboxylic acid transporter, wherein the transporter is selected from:
(a) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or 4, or the mature polypeptide sequence thereof;
(b) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing;
(c) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or 3, or the mature polypeptide coding sequence thereof;
(d) a C4-dicarboxylic acid transporter variant comprising a substitution, deletion, and/or insertion of one or more (e.g., two, several) amino acids of SEQ ID NO: 2 or 4, or the mature polypeptide sequence thereof; and
(e) a fragment of a C4-dicarboxylic acid transporter of (a), (b), (c), or (d) that has C4-dicarboxylic acid transporter activity;
wherein the host cell secretes increased levels of C4-dicarboxylic acid compared to the host cell without the heterologous polynucleotide when cultivated under the same conditions.
[50] A host cell comprising a heterologous polynucleotide encoding a C4-dicarboxylic acid transporter, wherein the transporter is selected from:
(a) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide sequence thereof;
(b) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 1, the mature polypeptide coding sequence thereof, or the full-length complementary strand of the foregoing;
(c) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or the mature polypeptide coding sequence thereof;
(d) a C4-dicarboxylic acid transporter variant comprising a substitution, deletion, and/or insertion of one or more (e.g., two, several) amino acids of SEQ ID NO: 2 or the mature polypeptide sequence thereof; and
(e) a fragment of a C4-dicarboxylic acid transporter of (a), (b), (c), or (d) that has C4-dicarboxylic acid transporter activity;
wherein the host cell secretes increased levels of C4-dicarboxylic acid compared to the host cell without the heterologous polynucleotide when cultivated under the same conditions.
[51] A host cell comprising a heterologous polynucleotide encoding a C4-dicarboxylic acid transporter, wherein the transporter is selected from:
(a) a C4-dicarboxylic acid transporter having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof;
(b) a C4-dicarboxylic acid transporter encoded by a polynucleotide that hybridizes under low stringency conditions, medium stringency conditions, medium-high stringency conditions, high stringency conditions, or very high stringency conditions with SEQ ID NO: 3, the mature polypeptide coding sequence thereof, or the full-length complementary strand of the foregoing;
(c) a C4-dicarboxylic acid transporter encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the mature polypeptide coding sequence thereof;

(d) a C4-dicarboxylic acid transporter variant comprising a substitution, deletion, and/or insertion of one or more (e.g., two, several) amino acids of SEQ ID NO: 4 or the mature polypeptide sequence thereof; and (e) a fragment of a C4-dicarboxylic acid transporter of (a), (b), (c), or (d) that has C4-dicarboxylic acid transporter activity;

wherein the host cell secretes increased levels of C4-dicarboxylic acid compared to the host cell without the heterologous polynucleotide when cultivated under the same conditions.

[52] The host cell of any one of paragraphs [49]-[51], wherein the C4-dicarboxylic acid transporter has at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 or 4, or the mature polypeptide sequence thereof.

[53] The host cell of any one of paragraphs [49]-[52], wherein the C4-dicarboxylic acid transporter is encoded by a polynucleotide that hybridizes under low stringency conditions, low-medium stringency conditions, medium stringency conditions, medium-high stringency conditions, high stringency conditions, or very high stringency conditions with SEQ ID NO: 1 or 3, the mature polypeptide coding sequence thereof, or a full-length complementary strand of the foregoing.

[54] The host cell of any one of paragraphs [49]-[53], wherein the C4-dicarboxylic acid transporter is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1 or 3, or the mature polypeptide coding sequence thereof.

[55] The host cell of any one of paragraphs [49]-[54], wherein the C4-dicarboxylic acid transporter comprises or consists of SEQ ID NO: 2 or 4.

[56] The host cell of any one of paragraphs [49]-[54], wherein the C4-dicarboxylic acid transporter comprises or consists of the mature polypeptide sequence of SEQ ID NO: 2.

[57] The host cell of paragraph [56], wherein the mature polypeptide sequence of SEQ ID NO: 2 is amino acids 53 to 392 of SEQ ID NO: 2.

[58] The host cell of paragraph [56] or [57], wherein the mature polypeptide sequence of SEQ ID NO: 4 is amino acids 1 to 393 of SEQ ID NO: 4.

[59] The host cell of any one of paragraphs [49]-[54], wherein the C4-dicarboxylic acid transporter is a fragment of SEQ ID NO: 2 or 4, wherein the fragment has C4-dicarboxylic acid transporter activity.

[60] The host cell of any one of paragraphs [49]-[54], wherein the C4-dicarboxylic acid transporter is a variant comprising a substitution, deletion, and/or insertion of one or more (e.g., two, several) amino acids of the mature polypeptide sequence of SEQ ID NO: 2 or 4.

[61] The host cell of any one of paragraphs [49]-[60], wherein the heterologous polynucleotide encoding the C4-dicarboxylic acid transporter is operably linked to a promoter foreign to the polynucleotide.

[62] The host cell of any one of paragraphs [49]-[61], wherein the host cell further comprises a heterologous second polynucleotide encoding a malate dehydrogenase (e.g., the malate dehydrogenase of SEQ ID NO: 11, or any described aspect thereof).

[63] The host cell of paragraph [62], wherein the heterologous second polynucleotide encoding a malate dehydrogenase is operably linked to a promoter foreign to the polynucleotide.

[64] The host cell of any one of paragraphs [49]-[63], wherein the host cell further comprises a heterologous third polynucleotide encoding a pyruvate carboxylase (e.g., the pyruvate carboxylase of SEQ ID NO: 13, or any described aspect thereof).

[65] The host cell of paragraph [64], wherein the heterologous third polynucleotide encoding a pyruvate carboxylase is operably linked to a promoter foreign to the polynucleotide.

[66] The host cell of any one of paragraphs [49]-[64], wherein the host cell is a filamentous fungal host cell.

[67] The filamentous fungal host cell of paragraph [66], wherein the host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes,* and *Trichoderma* cell.

[68] The filamentous fungal host cell of paragraph [67], wherein the host cell is an *Aspergillus* host cell.

[69] The filamentous fungal host cell of paragraph [68], wherein the host cell is an *Aspergillus oryzae* host cell.

[70] The host cell of any one of paragraphs [49]-[69], wherein the host cell is capable of secreting an increased level of the malic acid of at least 25%, e.g., at least 50%, at least 100%, at least 150%, at least 200%, at least 300%, or at 500% compared to the host cell without the polynucleotide encoding the heterologous polynucleotide when cultivated under the same conditions.

[71] The host cell of any one of paragraphs [49]-[70], wherein the C4-dicarboxylic acid is selected from malic acid, succinic acid, oxaloacetic acid, malonic acid, and fumaric acid.

[72] The host cell of paragraph [71], wherein the C4-dicarboxylic acid is malic acid.

What is claimed is:

1. An *Aspergillus oryzae* host cell comprising a heterologous polynucleotide encoding a C4-dicarboxylic acid transporter, wherein the heterologous polynucleotide:

(a) encodes a C4-dicarboxylic acid transporter having at least 95% sequence identity to SEQ ID NO: 2, or the mature polypeptide sequence thereof;

(b) hybridizes under high stringency conditions with the full-length complementary strand of SEQ ID NO: 1; or (c) has at least 95% sequence identity to SEQ ID NO: 1, or the mature polypeptide coding sequence thereof;

wherein the host cell is capable of secreting at least 50% more C4-dicarboxylic acid compared to the host cell without the heterologous polynucleotide encoding the C4-dicarboxylic acid transporter when cultivated under the same conditions.

2. The host cell of claim 1, wherein the heterologous polynucleotide encodes a C4-dicarboxylic acid transporter that comprises or consists of amino acids 53 to 392 of SEQ ID NO: 2.

3. The host cell of claim 1, wherein the heterologous polynucleotide encodes a C4-dicarboxylic acid transporter that comprises or consists of SEQ ID NO: 2.

4. The host cell of claim 1, wherein the heterologous polynucleotide encoding the C4-dicarboxylic acid transporter is operably linked to a promoter foreign to the polynucleotide.

5. The host cell of claim 1, wherein the C4-dicarboxylic acid is malic acid.

6. The host cell of claim 1, wherein the heterologous polynucleotide encodes a C4-dicarboxylic acid transporter having at least 95% sequence identity to amino acids 53 to 392 of SEQ ID NO: 2.

7. The host cell of claim 1, wherein the heterologous polynucleotide encodes a C4-dicarboxylic acid transporter having at least 97% sequence identity to amino acids 53 to 392 of SEQ ID NO: 2.

8. The host cell of claim 1, wherein the heterologous polynucleotide encodes a C4-dicarboxylic acid transporter having at least 99% sequence identity to amino acids 53 to 392 of SEQ ID NO: 2.

9. The host cell of claim 1, wherein the heterologous polynucleotide hybridizes under high stringency conditions with the full-length complementary strand of SEQ ID NO: 1.

10. The host cell of claim 1, wherein the heterologous polynucleotide hybridizes under very high stringency conditions with the full-length complementary strand of SEQ ID NO: 1.

11. The host cell of claim 1, wherein the heterologous polynucleotide has at least 95% sequence identity to nucleotides 157 to 1179 of SEQ ID NO: 1.

12. The host cell of claim 1, wherein the heterologous polynucleotide has at least 97% sequence identity to nucleotides 157 to 1179 of SEQ ID NO: 1.

13. The host cell of claim 1, wherein the heterologous polynucleotide has at least 99% sequence identity to nucleotides 157 to 1179 of SEQ ID NO: 1.

14. The host cell of claim 1, wherein the heterologous polynucleotide comprises or consists of nucleotides 157 to 1179 of SEQ ID NO: 1.

15. The host cell of claim 1, wherein the heterologous polynucleotide comprises or consists of SEQ ID NO: 1.

16. The host cell of claim 1, wherein the host cell is capable of secreting at least 100% more C4-dicarboxylic acid compared to the host cell without the heterologous polynucleotide encoding the C4-dicarboxylic acid transporter when cultivated under the same conditions.

17. A method of producing a C4-dicarboxylic acid, comprising:
(a) cultivating the host cell of claim 1 in a medium; and
(b) recovering the C4-dicarboxylic acid.

18. The method of claim 17, wherein the C4 dicarboxylic acid is malic acid.

* * * * *

SEQUENCE LISTING

<160> NUMBER OF SEQ ID NOS: 16

<210> SEQ ID NO 1
<211> LENGTH: 1179
<212> TYPE: DNA
<213> ORGANISM: Aspergillus clavatus

<400> SEQUENCE: 1

```
atgttcgaaa atcgtatacc gccgacctcg tctcagtcag actctggctt cctcgagaac    60
cagctggaaa acaacatcg actcagcctc cgtgagaggt taaggcactt tacctgggcc    120
tggtacacat tgaccatgag cacaggtggg ttggctctcc tgatagcgag ccagccatac    180
accttcaagg ggttgaagac cattggactg gtggtctaca tcgtgaactt gatcttgttt    240
ggtcttgtct gttcccttat ggccactagg ttcatcctcc acggtggctt cctcgactcc    300
cttcgccatg agcgcgaggg tctttttcttt cctaccttct ggctatccgt agcaaccatc    360
atcaccggct tgcatcgcta cttcggctcc gatgctcgag aatcgtacct gattgcactc    420
gaagtactct tctgggtcta ctgtgcctgt acactggcca cagcagtgat ccagtactcc    480
ttcatcttct ctgcgcacag atacggcctc cagaccatga tgccctcctg gattctccca    540
gccttcccca tcatgctcag tggcacgatt gcctccgtca tcggcgaagc tcaacccgca    600
cggtcatcga tccccgtcat catggccgga gtcaccttcc agggcctggg gttctcgatc    660
agcttcatga tgtacgccca ctatatcggc cggctgatgg aatcagggct cccctgccgc    720
gagcacagac ccggcatgtt catctgcgtt ggtcccccgg ctttcacagc cctcgctcta    780
gtcgggatgg ccaagggcct gcccgccgag ttcaagctca tcaacgacgc acacgccctc    840
gaagacgcgc ggatcctcga gctgctcgca atcaccgcgg gcatcttcct ctgggccctg    900
agtctgtggt tcttcttcat cgccgtcatc gccgtcctcc ggtccccgcc tacttccttc    960
catctcaact ggtgggcctt ggtcttcccg aacacgggct tcactttggc caccatcacg   1020
cttggaaagg cattgggcag tcccgggatc ttgggcgttg ttctgccat gtcccttggc   1080
atcgttggca tgtggctgtt tgttttttgtc agccatatcc gtgccatcat caaccaggat   1140
atcatgtatc cgggcaaaga tgaggatgct gcagactag                          1179
```

<210> SEQ ID NO 2
<211> LENGTH: 392
<212> TYPE: PRT
<213> ORGANISM: Aspergillus clavatus

<400> SEQUENCE: 2

```
Met Phe Glu Asn Arg Ile Pro Pro Thr Ser Gln Ser Asp Ser Gly
1               5                   10                  15

Phe Leu Glu Asn Gln Leu Glu Lys Gln His Arg Leu Ser Leu Arg Glu
            20                  25                  30

Arg Leu Arg His Phe Thr Trp Ala Trp Tyr Thr Leu Thr Met Ser Thr
        35                  40                  45

Gly Gly Leu Ala Leu Leu Ile Ala Ser Gln Pro Tyr Thr Phe Lys Gly
    50                  55                  60

Leu Lys Thr Ile Gly Leu Val Val Tyr Ile Val Asn Leu Ile Leu Phe
65                  70                  75                  80

Gly Leu Val Cys Ser Leu Met Ala Thr Arg Phe Ile Leu His Gly Gly
                85                  90                  95

Phe Leu Asp Ser Leu Arg His Glu Arg Glu Gly Leu Phe Phe Pro Thr
            100                 105                 110

Phe Trp Leu Ser Val Ala Thr Ile Ile Thr Gly Leu His Arg Tyr Phe
        115                 120                 125

Gly Ser Asp Ala Arg Glu Ser Tyr Leu Ile Ala Leu Glu Val Leu Phe
    130                 135                 140

Trp Val Tyr Cys Ala Cys Thr Leu Ala Thr Ala Val Ile Gln Tyr Ser
145                 150                 155                 160
```

```
Phe Ile Phe Ser Ala His Arg Tyr Gly Leu Gln Thr Met Met Pro Ser
                165                 170                 175

Trp Ile Leu Pro Ala Phe Pro Ile Met Leu Ser Gly Thr Ile Ala Ser
            180                 185                 190

Val Ile Gly Glu Ala Gln Pro Ala Arg Ser Ser Ile Pro Val Ile Met
        195                 200                 205

Ala Gly Val Thr Phe Gln Gly Leu Gly Phe Ser Ile Ser Phe Met Met
    210                 215                 220

Tyr Ala His Tyr Ile Gly Arg Leu Met Glu Ser Gly Leu Pro Cys Arg
225                 230                 235                 240

Glu His Arg Pro Gly Met Phe Ile Cys Val Gly Pro Ala Phe Thr
                245                 250                 255

Ala Leu Ala Leu Val Gly Met Ala Lys Gly Leu Pro Ala Glu Phe Lys
                260                 265                 270

Leu Ile Asn Asp Ala His Ala Leu Glu Asp Ala Arg Ile Leu Glu Leu
            275                 280                 285

Leu Ala Ile Thr Ala Gly Ile Phe Leu Trp Ala Leu Ser Leu Trp Phe
        290                 295                 300

Phe Phe Ile Ala Val Ile Ala Val Leu Arg Ser Pro Pro Thr Ser Phe
305                 310                 315                 320

His Leu Asn Trp Trp Ala Leu Val Phe Pro Asn Thr Gly Phe Thr Leu
                325                 330                 335

Ala Thr Ile Thr Leu Gly Lys Ala Leu Gly Ser Pro Gly Ile Leu Gly
                340                 345                 350

Val Gly Ser Ala Met Ser Leu Gly Ile Val Gly Met Trp Leu Phe Val
            355                 360                 365

Phe Val Ser His Ile Arg Ala Ile Ile Asn Gln Asp Ile Met Tyr Pro
    370                 375                 380

Gly Lys Asp Glu Asp Ala Ala Asp
385                 390
```

<210> SEQ ID NO 3
<211> LENGTH: 1182
<212> TYPE: DNA
<213> ORGANISM: Aspergillus fumigatus

<400> SEQUENCE: 3

| | | | | | |
|---|---|---|---|---|---|
| atgttcaacg | atcatgatca | tgttccacca | acatcatcac | agtcggattc | tggctttttt | 60 |
| gaacaagaaa | tgaagaaatc | tcctcgacta | agccttcgtg | agcgcctacg | gcacttcacc | 120 |
| tgggcgtggt | ataccttgac | gatgagtacc | ggtggactgg | ctcttctgat | tgctagtcag | 180 |
| ccgtatacct | tcaatggcat | gaagggcatc | gggatggtcg | tttatatcct | caatcttctg | 240 |
| ttattcgctc | ttgtctgttc | tttgatggtg | ctgagattcg | ttttgcatgg | cggtttcctt | 300 |
| gacagcttgc | gccaccctcg | cgagggtctc | ttcttcccta | ccttctggct | atccattgca | 360 |
| acgatcatca | ctggcttgca | tcgttacttc | ggctccgacg | acctagagtc | gtacctcatc | 420 |
| gcactcgaag | tcctcttctg | ggtctactgt | agttgcaccc | tcgccacagc | tgtgatccag | 480 |
| tactcattcc | tctttgccgc | ccactcctac | ggcctgcaga | caatgatgcc | atcatggatc | 540 |
| ctaccagcct | tccccatcat | gctcagcgga | accatcgcct | cggtcatcag | cgaatcccag | 600 |
| cccgcgcgat | ccgcgatccc | catcatcact | gccggcgtta | ccttccaggg | cctcggcttc | 660 |
| tcaatcagct | tcataatgta | cgcccactac | atcggccgac | tcatgcagtc | agggcttccc | 720 |
| tgccgcgaac | acagaccagc | catgttcatt | tgcgtggggc | ctccgtcttt | caccgcgttg | 780 |

```
gcgctagtag ggatggccaa gggcctgccc gacgaattca agataatcaa agacgcacac    840
gtcgaggacg cccggatcct cgagctgatg gctattatcg tcggcgtgtt cctgtgggcc    900
ctgagtctct ggttcttctt cattgccttt gttgctgtcg tccggtgccg gcccactgcg    960 ttccaccttta gctggtgggc catggtcttc cccaacactg ggttcacgct ggccactatt   1020
accctgggga gggcattggg gagccctggc gtcttgggcg tcggctcggc catgtcggtc    1080
ggtgttgtct gcatgtgggt cttcgttttc gtctaccaca ttcgtgctgt catcaggcaa    1140
gacatcatgt acccgggcaa agacgaggat gtgctagatt aa                      1182
```

<210> SEQ ID NO 4
<211> LENGTH: 393
<212> TYPE: PRT
<213> ORGANISM: Aspergillus fumigatus

<400> SEQUENCE: 4

```
Met Phe Asn Asp His Asp His Val Pro Pro Thr Ser Ser Gln Ser Asp
1               5                   10                  15

Ser Gly Phe Phe Glu Gln Glu Met Lys Lys Ser Pro Arg Leu Ser Leu
            20                  25                  30

Arg Glu Arg Leu Arg His Phe Thr Trp Ala Trp Tyr Thr Leu Thr Met
        35                  40                  45

Ser Thr Gly Gly Leu Ala Leu Leu Ile Ala Ser Gln Pro Tyr Thr Phe
    50                  55                  60

Asn Gly Met Lys Gly Ile Gly Met Val Val Tyr Ile Leu Asn Leu Leu
65                  70                  75                  80

Leu Phe Ala Leu Val Cys Ser Leu Met Val Leu Arg Phe Val Leu His
                85                  90                  95

Gly Gly Phe Leu Asp Ser Leu Arg His Pro Arg Glu Gly Leu Phe Phe
            100                 105                 110

Pro Thr Phe Trp Leu Ser Ile Ala Thr Ile Ile Thr Gly Leu His Arg
        115                 120                 125

Tyr Phe Gly Ser Asp Asp Leu Glu Ser Tyr Leu Ile Ala Leu Glu Val
    130                 135                 140

Leu Phe Trp Val Tyr Cys Ser Cys Thr Leu Ala Thr Ala Val Ile Gln
145                 150                 155                 160

Tyr Ser Phe Leu Phe Ala Ala His Ser Tyr Gly Leu Gln Thr Met Met
                165                 170                 175

Pro Ser Trp Ile Leu Pro Ala Phe Pro Ile Met Leu Ser Gly Thr Ile
            180                 185                 190

Ala Ser Val Ile Ser Glu Ser Gln Pro Ala Arg Ser Ala Ile Pro Ile
        195                 200                 205

Ile Thr Ala Gly Val Thr Phe Gln Gly Leu Gly Phe Ser Ile Ser Phe
    210                 215                 220

Ile Met Tyr Ala His Tyr Ile Gly Arg Leu Met Gln Ser Gly Leu Pro
225                 230                 235                 240

Cys Arg Glu His Arg Pro Ala Met Phe Ile Cys Val Gly Pro Pro Ser
                245                 250                 255

Phe Thr Ala Leu Ala Leu Val Gly Met Ala Lys Gly Leu Pro Asp Glu
            260                 265                 270

Phe Lys Ile Ile Lys Asp Ala His Val Glu Asp Ala Arg Ile Leu Glu
        275                 280                 285

Leu Met Ala Ile Ile Val Gly Val Phe Leu Trp Ala Leu Ser Leu Trp
    290                 295                 300

Phe Phe Phe Ile Ala Phe Val Ala Val Val Arg Cys Arg Pro Thr Ala
```

```
                305                 310                 315                 320
Phe His Leu Ser Trp Trp Ala Met Val Phe Pro Asn Thr Gly Phe Thr
                    325                 330                 335

Leu Ala Thr Ile Thr Leu Gly Arg Ala Leu Gly Ser Pro Gly Val Leu
            340                 345                 350

Gly Val Gly Ser Ala Met Ser Val Gly Val Val Cys Met Trp Val Phe
        355                 360                 365

Val Phe Val Tyr His Ile Arg Ala Val Ile Arg Gln Asp Ile Met Tyr
    370                 375                 380

Pro Gly Lys Asp Glu Asp Val Leu Asp
385                 390

<210> SEQ ID NO 5
<211> LENGTH: 36
<212> TYPE: DNA
<213> ORGANISM: Aspergillus clavatus

<400> SEQUENCE: 5
gtgtgataga acatcgtcca taatgttcga aaatcg                              36

<210> SEQ ID NO 6
<211> LENGTH: 44
<212> TYPE: DNA
<213> ORGANISM: Aspergillus clavatus

<400> SEQUENCE: 6
gtcagtcacc tctagttaat taactagtct gcagcatcct catc                     44

<210> SEQ ID NO 7
<211> LENGTH: 25
<212> TYPE: DNA
<213> ORGANISM: Aspergillus clavatus

<400> SEQUENCE: 7
ctatagcgaa atggattgat tgtct                                          25

<210> SEQ ID NO 8
<211> LENGTH: 20
<212> TYPE: DNA
<213> ORGANISM: Aspergillus clavatus

<400> SEQUENCE: 8
tgaccttcca cgctgaccac                                                20

<210> SEQ ID NO 9
<211> LENGTH: 42
<212> TYPE: DNA
<213> ORGANISM: Aspergillus fumigates

<400> SEQUENCE: 9
gtgtgataga acatcgtcca taatgttcaa cgatcatgat ca                       42

<210> SEQ ID NO 10
<211> LENGTH: 44
<212> TYPE: DNA
<213> ORGANISM: Aspergillus fumigates

<400> SEQUENCE: 10
gtcagtcacc tctagttaat taattaatct agcacatcct cgtc                     44

<210> SEQ ID NO 11
<211> LENGTH: 1430
```

```
<212> TYPE: DNA
<213> ORGANISM: Aspergillus oryzae

<400> SEQUENCE: 11
atggtcaaag ctggtgagtt agcaatcctt aacagatgac actctcatag gtactaactc      60
gaaacgttag cggtacttgg agcttctggt ggcattggcc aggtatggat atccccacgc     120
cttacaaccc tggtcacaat atgaccttgt tcgatactga ctatctccca agccactgtc     180
tctcctgttg aagacctgtc ccttagttga agagcttgct ctctacgatg ttgtgaacac     240
ccctggtgtt gctgctgatc tatcccacat ctcgtctatc gctgtacgtt actgccacaa     300
tgcgaattgc ccgatggaag aggcgaaaaa tggtatcttg cttacctggg cgattagaaa     360
atctctggtt ttctgcccaa agatgatggg ctgaagcagg cccttactgg tgctaatatt     420
gttgtcatcc cggctggtat tccccgtaag tccctaccct ttcgcattgc tcctcgtatg     480
ttcgctggtg ccagttttc tgatagttga taggcaagcc tggtatgacc cgtgacgacc       540
tcttcaagat caacgccggc atagtgcgag acttggtcaa gggtatcgcc gagttctgcc     600
ccaaggcctt tgttctggtt atctcaaacc ccgttaattc tactgttcct attgctgcag     660
aggtgctcaa agccgctggc gtctttgacc cgaagcgcct ctttggtgtc accacactgg     720
acgtcgttcg tgcagagact ttcacccaag agttctcggg ccagaaggat ccttctgctg     780
ttcaaatccc agttgttggt ggccactctg gagagaccat tgtcccccctc ttcagcaaga     840
ctaccccccgc aattcagata cccgaggaga gtatgacgc actgatccac cgtaggttgt      900
cccaaagaat ctcatgaata tcttgctgta agcactaact atgcttcagg cgtccaattt     960
ggtggagatg aggtggtcca agctaaggac ggtgctggtt ccgccacctt gtctatggcc    1020
tatgccggtt acaggtaggg atgctgcgta ccgtgagagc actcgcggct aacatgccat    1080
aggttcgctg agagtgtaat caaagcttca aagggtcaaa cgggtattgt cgagcctacc    1140
ttcgtctacc tgcctggaat tcccggcggt gatgagatcg ttaaggcaac tggcgtggaa    1200
ttcttctcta ctcttgtaac cttaggagta agattcatct cctcacagaa tcttcgttca    1260
tatcacgcca ggctaacgct attaaacaga ctaatggcgc agagaaggct agcaacgttc    1320
ttgagggcgt gaccgagaag gaaaagaagc ttctcgaggc ttgcacgaaa ggccttaagg    1380
gtaatatcga gaaggcatc gacttcgtta agaacccacc accaaagtaa              1430

<210> SEQ ID NO 12
<211> LENGTH: 330
<212> TYPE: PRT
<213> ORGANISM: Aspergillus oryzae

<400> SEQUENCE: 12

Met Val Lys Ala Ala Val Leu Gly Ala Ser Gly Gly Ile Gly Gln Pro
1               5                   10                  15

Leu Ser Leu Leu Leu Lys Thr Cys Pro Leu Val Glu Glu Leu Ala Leu
            20                  25                  30

Tyr Asp Val Val Asn Thr Pro Gly Val Ala Ala Asp Leu Ser His Ile
        35                  40                  45

Ser Ser Ile Ala Lys Ile Ser Gly Phe Leu Pro Lys Asp Asp Gly Leu
    50                  55                  60

Lys Gln Ala Leu Thr Gly Ala Asn Ile Val Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Lys Gly Ile Ala Glu Phe Cys Pro Lys
```

```
            100                 105                 110
Ala Phe Val Leu Val Ile Ser Asn Pro Val Asn Ser Thr Val Pro Ile
            115                 120                 125

Ala Ala Glu Val Leu Lys Ala Ala Gly Val Phe Asp Pro Lys Arg Leu
            130                 135                 140

Phe Gly Val Thr Thr Leu Asp Val Val Arg Ala Glu Thr Phe Thr Gln
145                 150                 155                 160

Glu Phe Ser Gly Gln Lys Asp Pro Ser Ala Val Gln Ile Pro Val Val
                165                 170                 175

Gly Gly His Ser Gly Glu Thr Ile Val Pro Leu Phe Ser Lys Thr Thr
            180                 185                 190

Pro Ala Ile Gln Ile Pro Glu Glu Lys Tyr Asp Ala Leu Ile His Arg
            195                 200                 205

Val Gln Phe Gly Gly Asp Glu Val Val Gln Ala Lys Asp Gly Ala Gly
            210                 215                 220

Ser Ala Thr Leu Ser Met Ala Tyr Ala Gly Tyr Arg Phe Ala Glu Ser
225                 230                 235                 240

Val Ile Lys Ala Ser Lys Gly Gln Thr Gly Ile Val Glu Pro Thr Phe
                245                 250                 255

Val Tyr Leu Pro Gly Ile Pro Gly Gly Asp Glu Ile Val Lys Ala Thr
            260                 265                 270

Gly Val Glu Phe Phe Ser Thr Leu Val Thr Leu Gly Thr Asn Gly Ala
            275                 280                 285

Glu Lys Ala Ser Asn Val Leu Glu Gly Val Thr Glu Lys Glu Lys Lys
            290                 295                 300

Leu Leu Glu Ala Cys Thr Lys Gly Leu Lys Gly Asn Ile Glu Lys Gly
305                 310                 315                 320

Ile Asp Phe Val Lys Asn Pro Pro Lys
                325                 330

<210> SEQ ID NO 13
<211> LENGTH: 3643
<212> TYPE: DNA
<213> ORGANISM: Aspergillus oryzae

<400> SEQUENCE: 13
atggcggctc cgtttcgtca gcctgaggag gcggtcgatg acaccgagtt catcgatgac      60
caccatgaac acctccgtga taccgtgcac catcggttgc gcgccaattc ctccattatg     120
cacttccaga agatcctcgt cgccaaccgt ggtgagatcc ccattcgtat cttcagaacg     180
gcccacgagc tgtcattgca gacggttgct atctactctc atgaggatcg actgtcaatg     240
caccgtcaaa aggccgatga ggcctacatg attggccacc gcggtcagta caccccctgtc    300 ggtgcgtacc tggcgggcga tgagatcatc aagatcgccc tggagcacgg tgtccagctg     360
atccacccgg gctacggttt cttgtccgag aacgccgact cgcccgcaa ggttgagaac      420 gccggcattg tctttgtggg acccactccc gataccattg acagcttggg tgacaaggtg    480
tcggcccgtc ggctggccat taagtgcgag gtccctgtcg ttccgggtac ggagggcccc    540
gtcgagcgct atgaggaggt caaggcgttc acagacacct atggcttccc catcatcatc    600
aaggctgcct ttggcggtgg tggccgtggt atgcgtgtgg tccgtgacca ggccgagctg    660
cgtgactcgt tcgagcgagc cacctctgag gcccgctccg ccttcggcaa tggtaccgtc    720
ttcgtcgagc gcttcctcga caaacccaag cacattgaag tccagcttct gggtgacagc    780
cacggcaacg ttgtccatct gtttgagcgt gactgctccg tgcagcgtcg tcaccagaag    840
```

```
gtcgttgagg ttgctccggc taaggacctg ccagccgatg tccgggaccg catcctggcc   900
gatgctgtga agctggccaa gtccgtcaac taccgtaacg ccggtacagc tgagttcctg   960
gtggaccagc agaaccgcca ctacttcatt gaaatcaatc ctcgtatcca agtcgagcac  1020
accatcaccg aagagattac tggtatcgat atcgtggctg cacagatcca gattgctgct  1080
ggtgcaagcc tcgagcaact gggcctgact caggaccgca tctccgcccg cggatttgcc  1140
attcaatgtc gtatcaccac ggaagatccc gccaagggt tctctccgga tactggtaag  1200
attgaggttt atcgttccgc tggtggtaac ggtgtccgtc tggatggtgg taacggtttc  1260
gctggtgcta tcatcacccc tcactacgac tccatgctgg tcaagtgtac ctgccgtggt  1320
tcgacctatg aaatcgctcg tcgcaaggtt gtgcgtgcct tggtcgagtt ccgtattcgt  1380
ggtgtgaaga ccaacattcc cttcctgact tcgcttctga ccacccgac cttcgtcgat  1440
ggaaactgct ggaccacttt catcgacgac acccctgaat tgttctctct tgtcggcagt  1500
cagaaccgtg cccagaagct gctcgcatac ctcggcgatg tagctgtcaa cggtagtagc  1560
atcaagggcc aaattggcga gcccaagctc aagggtgatg tcatcaagcc gaagcttttc  1620
gatgccgagg gcaagccgct tgacgttttc gcccccgtgca ccaaggggttg aagcagatt  1680
ctggaccggg agggcccggc tgcctttgcg aaggccgtgc gtgccaacaa gggttgcttg  1740
atcatggata ctacctggcg tgacgcccac cagtctttgc tggccacccg tgtgcgtacc  1800
atcgacttgt tgaacatcgc ccatgagacc agctacgcct actccaatgc gtacagtttg  1860
gaatgctggg gtggtgctac cttcgatgtg ccatgcgtt tcctctatga ggacccctgg  1920
gaccgcctgc gcaagatgcg taaggctgtt cctaacatcc cattccagat gttgctccgt  1980
ggtgccaacg tgtcgcccta ctcttccctc ccagacaacg ccatctacca cttctgtaag  2040
caggctaaga agtgcggtgt cgacattttc cgtgttttcg acgccctcaa cgatgtcgat  2100
cagctcgagg tcggtatcaa ggctgttcat gctgccgagg gtgttgtcga ggccaccatg  2160
tgctacagcg gtgacatgct gaaccccac aagaagtaca acctggagta ctacatggcc  2220
ttggtggata agattgtagc catgaagcct cacatccttg gtatcaagga tatggccggt  2280
gtgctgaagc cccaggccgc tcgcctgttg gtgggctcca tccgtcagcg ctaccctgac  2340
cttcccatcc acgtccacac ccacgactcc gctggtactg gtgtagcttc catgattgcc  2400
tgtgcccagg cgggtgccga cgccgtggac gccgcgaccg acagcatgtc cggtatgacc  2460
tcccagccta gcattggtgc cattctggcc tctcttgagg gcactgagca agaccccggt  2520
ctcaacctcg cccacgtgcg cgctattgat agctactggg cacagctgcg cttgctctac  2580
tctcctttcg aggcgggtct cactggcccc gaccctgagg tctacgagca cgagatccct  2640
ggtggtcagt tgaccaacct tatcttccag gccagtcagc tcggcttggg ccagcagtgg  2700
gccgaaacca gaaggccta tgaggcggct aatgatttac tcggcgacat tgtaaaggtc  2760
actcccacct ccaaggtggt cggtgacttg gctcagttca tggtctcgaa caaactgact  2820
ccggaggatg ttgttgagcg tgctggtgag ctggacttcc ctggttctgt gctcgaattc  2880
ctcgaaggtc tcatgggaca gcccttcggt ggattcccg agccattgcg ctcccgcgcc  2940
ctgcgcgatc gccgcaagct cgagaagcgt ccaggtctct acctcgagcc tttggatttg  3000
gctaagatca agagccagat ccgtgagaag ttcggtgctg ctactgagta tgacgtggcc  3060
agctatgcca tgtatcccaa ggtcttcgag gactacaaga agttcgtcca agttcggt  3120
gatctctccg tcttgcccac acggtacttc ttggccaagc tgagattgg cgaggagttc  3180
cacgttgagc tggagaaggg taaggtgctc atcctgaagt tgttggccat cggccctctt  3240
```

```
tcagagcaga ctggtcagcg tgaggtcttc tacgaagtca acggtgaggt gcgccaggtc     3300
gctgttgatg acaacaaggc ttccgtggac aacacttcac gccctaaggc cgatgtgggt     3360
gacagcagcc aggtcggtgc tcctatgagc ggtgtggttg ttgaaatccg tgtccacgat     3420
ggtctggagg ttaagaaggg tgacccactt gccgtcctga gtgccatgaa gatggtaagt     3480
tcattccgaa tcattttttct cactggtcaa ctacagatgc taacagctta ccaggaaat      3540 ggttatctct gctcctcaca gtggaaaggt ctccagcttg ctggtcaagg agggcgattc     3600
tgtggatggc caggatctcg tctgcaagat cgtcaaagcg taa                       3643
```

<210> SEQ ID NO 14
<211> LENGTH: 1193
<212> TYPE: PRT
<213> ORGANISM: Aspergillus oryzae

<400> SEQUENCE: 14

```
Met Ala Ala Pro Phe Arg Gln Pro Glu Glu Ala Val Asp Asp Thr Glu
 1               5                  10                  15

Phe Ile Asp Asp His His Glu His Leu Arg Asp Thr Val His His Arg
                20                  25                  30

Leu Arg Ala Asn Ser Ser Ile Met His Phe Gln Lys Ile Leu Val Ala
             35                  40                  45

Asn Arg Gly Glu Ile Pro Ile Arg Ile Phe Arg Thr Ala His Glu Leu
         50                  55                  60

Ser Leu Gln Thr Val Ala Ile Tyr Ser His Glu Asp Arg Leu Ser Met
 65                  70                  75                  80

His Arg Gln Lys Ala Asp Glu Ala Tyr Met Ile Gly His Arg Gly Gln
                 85                  90                  95

Tyr Thr Pro Val Gly Ala Tyr Leu Ala Gly Asp Glu Ile Ile Lys Ile
            100                 105                 110

Ala Leu Glu His Gly Val Gln Leu Ile His Pro Gly Tyr Gly Phe Leu
        115                 120                 125

Ser Glu Asn Ala Asp Phe Ala Arg Lys Val Glu Asn Ala Gly Ile Val
    130                 135                 140

Phe Val Gly Pro Thr Pro Asp Thr Ile Asp Ser Leu Gly Asp Lys Val
145                 150                 155                 160

Ser Ala Arg Arg Leu Ala Ile Lys Cys Glu Val Pro Val Val Pro Gly
                165                 170                 175

Thr Glu Gly Pro Val Glu Arg Tyr Glu Glu Val Lys Ala Phe Thr Asp
            180                 185                 190

Thr Tyr Gly Phe Pro Ile Ile Ile Lys Ala Ala Phe Gly Gly Gly Gly
        195                 200                 205

Arg Gly Met Arg Val Val Arg Asp Gln Ala Glu Leu Arg Asp Ser Phe
    210                 215                 220

Glu Arg Ala Thr Ser Glu Ala Arg Ser Ala Phe Gly Asn Gly Thr Val
225                 230                 235                 240

Phe Val Glu Arg Phe Leu Asp Lys Pro Lys His Ile Glu Val Gln Leu
                245                 250                 255

Leu Gly Asp Ser His Gly Asn Val Val His Leu Phe Glu Arg Asp Cys
            260                 265                 270

Ser Val Gln Arg His Gln Lys Val Glu Val Ala Pro Ala Lys
        275                 280                 285

Asp Leu Pro Ala Asp Val Arg Asp Arg Ile Leu Ala Asp Ala Val Lys
    290                 295                 300

Leu Ala Lys Ser Val Asn Tyr Arg Asn Ala Gly Thr Ala Glu Phe Leu
```

```
              305                 310                 315                 320
Val Asp Gln Gln Asn Arg His Tyr Phe Ile Glu Ile Asn Pro Arg Ile
                        325                 330                 335
Gln Val Glu His Thr Ile Thr Glu Glu Ile Thr Gly Ile Asp Ile Val
            340                 345                 350
Ala Ala Gln Ile Gln Ile Ala Ala Gly Ala Ser Leu Glu Gln Leu Gly
            355                 360                 365
Leu Thr Gln Asp Arg Ile Ser Ala Arg Gly Phe Ala Ile Gln Cys Arg
            370                 375                 380
Ile Thr Thr Glu Asp Pro Ala Lys Gly Phe Ser Pro Asp Thr Gly Lys
385                 390                 395                 400
Ile Glu Val Tyr Arg Ser Ala Gly Gly Asn Gly Val Arg Leu Asp Gly
                        405                 410                 415
Gly Asn Gly Phe Ala Gly Ala Ile Ile Thr Pro His Tyr Asp Ser Met
                420                 425                 430
Leu Val Lys Cys Thr Cys Arg Gly Ser Thr Tyr Glu Ile Ala Arg Arg
            435                 440                 445
Lys Val Val Arg Ala Leu Val Glu Phe Arg Ile Arg Gly Val Lys Thr
450                 455                 460
Asn Ile Pro Phe Leu Thr Ser Leu Leu Ser His Pro Thr Phe Val Asp
465                 470                 475                 480
Gly Asn Cys Trp Thr Thr Phe Ile Asp Asp Thr Pro Glu Leu Phe Ser
                        485                 490                 495
Leu Val Gly Ser Gln Asn Arg Ala Gln Lys Leu Leu Ala Tyr Leu Gly
                500                 505                 510
Asp Val Ala Val Asn Gly Ser Ser Ile Lys Gly Gln Ile Gly Glu Pro
            515                 520                 525
Lys Leu Lys Gly Asp Val Ile Lys Pro Lys Leu Phe Asp Ala Glu Gly
            530                 535                 540
Lys Pro Leu Asp Val Ser Ala Pro Cys Thr Lys Gly Trp Lys Gln Ile
545                 550                 555                 560
Leu Asp Arg Glu Gly Pro Ala Ala Phe Ala Lys Ala Val Arg Ala Asn
                        565                 570                 575
Lys Gly Cys Leu Ile Met Asp Thr Thr Trp Arg Asp Ala His Gln Ser
                580                 585                 590
Leu Leu Ala Thr Arg Val Arg Thr Ile Asp Leu Leu Asn Ile Ala His
            595                 600                 605
Glu Thr Ser Tyr Ala Tyr Ser Asn Ala Tyr Ser Leu Glu Cys Trp Gly
            610                 615                 620
Gly Ala Thr Phe Asp Val Ala Met Arg Phe Leu Tyr Glu Asp Pro Trp
625                 630                 635                 640
Asp Arg Leu Arg Lys Met Arg Lys Ala Val Pro Asn Ile Pro Phe Gln
                        645                 650                 655
Met Leu Leu Arg Gly Ala Asn Gly Val Ala Tyr Ser Ser Leu Pro Asp
                660                 665                 670
Asn Ala Ile Tyr His Phe Cys Lys Gln Ala Lys Lys Cys Gly Val Asp
            675                 680                 685
Ile Phe Arg Val Phe Asp Ala Leu Asn Asp Val Asp Gln Leu Glu Val
            690                 695                 700
Gly Ile Lys Ala Val His Ala Ala Glu Gly Val Val Glu Ala Thr Met
705                 710                 715                 720
Cys Tyr Ser Gly Asp Met Leu Asn Pro His Lys Lys Tyr Asn Leu Glu
                        725                 730                 735
```

```
Tyr Tyr Met Ala Leu Val Asp Lys Ile Val Ala Met Lys Pro His Ile
            740                 745                 750

Leu Gly Ile Lys Asp Met Ala Gly Val Leu Lys Pro Gln Ala Ala Arg
            755                 760                 765

Leu Leu Val Gly Ser Ile Arg Gln Arg Tyr Pro Asp Leu Pro Ile His
            770                 775                 780

Val His Thr His Asp Ser Ala Gly Thr Gly Val Ala Ser Met Ile Ala
785                 790                 795                 800

Cys Ala Gln Ala Gly Ala Asp Ala Val Asp Ala Ala Thr Asp Ser Met
                    805                 810                 815

Ser Gly Met Thr Ser Gln Pro Ser Ile Gly Ala Ile Leu Ala Ser Leu
                820                 825                 830

Glu Gly Thr Glu Gln Asp Pro Gly Leu Asn Leu Ala His Val Arg Ala
            835                 840                 845

Ile Asp Ser Tyr Trp Ala Gln Leu Arg Leu Leu Tyr Ser Pro Phe Glu
850                 855                 860

Ala Gly Leu Thr Gly Pro Asp Pro Glu Val Tyr Glu His Glu Ile Pro
865                 870                 875                 880

Gly Gly Gln Leu Thr Asn Leu Ile Phe Gln Ala Ser Gln Leu Gly Leu
                    885                 890                 895

Gly Gln Gln Trp Ala Glu Thr Lys Lys Ala Tyr Glu Ala Ala Asn Asp
                900                 905                 910

Leu Leu Gly Asp Ile Val Lys Val Thr Pro Thr Ser Lys Val Val Gly
            915                 920                 925

Asp Leu Ala Gln Phe Met Val Ser Asn Lys Leu Thr Pro Glu Asp Val
            930                 935                 940

Val Glu Arg Ala Gly Glu Leu Asp Phe Pro Gly Ser Val Leu Glu Phe
945                 950                 955                 960

Leu Glu Gly Leu Met Gly Gln Pro Phe Gly Gly Phe Pro Glu Pro Leu
                    965                 970                 975

Arg Ser Arg Ala Leu Arg Asp Arg Arg Lys Leu Glu Lys Arg Pro Gly
                980                 985                 990

Leu Tyr Leu Glu Pro Leu Asp Leu  Ala Lys Ile Lys Ser  Gln Ile Arg
            995                 1000                1005

Glu Lys  Phe Gly Ala Ala Thr  Glu Tyr Asp Val Ala  Ser Tyr Ala
    1010                1015                1020

Met Tyr Pro Lys Val Phe Glu  Asp Tyr Lys Lys Phe  Val Gln Lys
    1025                1030                1035

Phe Gly Asp Leu Ser Val Leu  Pro Thr Arg Tyr Phe  Leu Ala Lys
    1040                1045                1050

Pro Glu  Ile Gly Glu Glu Phe  His Val Glu Leu Glu  Lys Gly Lys
    1055                1060                1065

Val Leu Ile Leu Lys Leu Leu  Ala Ile Gly Pro Leu  Ser Glu Gln
    1070                1075                1080

Thr Gly  Gln Arg Glu Val Phe  Tyr Glu Val Asn Gly  Glu Val Arg
    1085                1090                1095

Gln Val  Ala Val Asp Asp Asn  Lys Ala Ser Val Asp  Asn Thr Ser
    1100                1105                1110

Arg Pro  Lys Ala Asp Val Gly  Asp Ser Ser Gln Val  Gly Ala Pro
    1115                1120                1125

Met Ser  Gly Val Val Val Glu  Ile Arg Val His Asp  Gly Leu Glu
    1130                1135                1140

Val Lys  Lys Gly Asp Pro Leu  Ala Val Leu Ser Ala  Met Lys Met
    1145                1150                1155
```

Glu Met Val Ile Ser Ala Pro His Ser Gly Lys Val Ser Ser Leu
    1160                1165                1170

Leu Val Lys Glu Gly Asp Ser Val Asp Gly Gln Asp Leu Val Cys
    1175                1180                1185

Lys Ile Val Lys Ala
    1190

<210> SEQ ID NO 15
<211> LENGTH: 1294
<212> TYPE: DNA
<213> ORGANISM: Aspergillus oryzae

<400> SEQUENCE: 15

```
atgttcgctg ctcgccagtc tttcaacctc ctccagaagc gcgccttctc cgcctctgcc      60
agccaggtgt gtgattgaat ggatccattg gacctcggag ctagctctgc aacatcaaca     120
aaactaacat actaacttat cttcttcata ggcttccaag gttgccgttc ttggtgccgc     180
tggtggcatt ggccagcctc tctcccttct cctcaagctc aaccccgtg tttctgagct      240
tgccctctac gatatccgcg gtggcccctgg tatgttttg cacagcttgc aacatctccg     300
acttcggtga ttcaagacag gctaacata aggatacaat aggtgttgcc gctgacctga     360
gccacatcaa caccaacagc accgtctctg gctacgaggc tacccctct ggcctccgtg      420
atgctctcaa gggctccgag atcgtcctca tccctgccgg tgttcctcgc aagcccggca     480
tgacccgtga cggtatgaac cgttaacttg tcaatggcac tgggaattga atactaatta     540
taatatcgcc agacctgttc aacaccaacg cctccattgt ccgcgacctt gctaaggccg     600
ccgccgaggc ttcccccgag gccaacatcc tcgtcatctc caaccctgta tgacgctttc     660
cacccactgc taccagttat ctcgcgctaa ttgcaatcag gtcaactcca ccgtcccat      720
cgtctctgag gtcttcaagt ccaagggtgt ctacaacccc aagcgtctct tcggtgtcac     780
tacccttgac gttgtccgtg cctctcgctt catctcccag gtccagaaga ccgacccctc     840
caacgaggcc gtcactgtcg tcggtggtca ctccggtgtg accattgtcc ctcttctctc     900
ccagtccagc caccccagca ttgagggtaa gaccgcgat gagctcgtca accgcatcca      960
gttcggtggt gatgaggttg tcaaggccaa ggatggtgct ggctctgcca ccctctccat    1020
ggccatggct ggtgctcgca tggctgagtc cctcctgaag gccgcccagg gtgagaaggg    1080
tgtcgttgag cccactttcg tcgacagccc tctctacaag gaccagggtg ttgacttctt    1140
cgcctccaag gtcgagctcg gccccaacgg tgttgagaag atcctccccg ttggccaggt    1200
caacgcctac gaggagaagc tcctcgaggc ctgccttggt gacctcaaga gaacatcca    1260
gaagggtatt gacttcgtca aggccaaccc ttaa                                1294
```

<210> SEQ ID NO 16
<211> LENGTH: 340
<212> TYPE: PRT
<213> ORGANISM: Aspergillus oryzae

<400> SEQUENCE: 16

Met Phe Ala Ala Arg Gln Ser Phe Asn Leu Leu Gln Lys Arg Ala Phe
1               5                   10                  15

Ser Ala Ser Ala Ser Gln Ala Ser Lys Val Ala Val Leu Gly Ala Ala
            20                  25                  30

Gly Gly Ile Gly Gln Pro Leu Ser Leu Leu Leu Lys Leu Asn Pro Arg
        35                  40                  45

Val Ser Glu Leu Ala Leu Tyr Asp Ile Arg Gly Gly Pro Gly Val Ala

-continued

```
                    50                  55                  60
Ala Asp Leu Ser His Ile Asn Thr Asn Ser Thr Val Ser Gly Tyr Glu
 65                  70                  75                  80

Ala Thr Pro Ser Gly Leu Arg Asp Ala Leu Lys Gly Ser Glu Ile Val
                 85                  90                  95

Leu Ile Pro Ala Gly Val Pro Arg Lys Pro Gly Met Thr Arg Asp Asp
                100                 105                 110

Leu Phe Asn Thr Asn Ala Ser Ile Val Arg Asp Leu Ala Lys Ala Ala
                115                 120                 125

Ala Glu Ala Ser Pro Glu Ala Asn Ile Leu Val Ile Ser Asn Pro Val
                130                 135                 140

Asn Ser Thr Val Pro Ile Val Ser Glu Val Phe Lys Ser Lys Gly Val
145                 150                 155                 160

Tyr Asn Pro Lys Arg Leu Phe Gly Val Thr Thr Leu Asp Val Val Arg
                165                 170                 175

Ala Ser Arg Phe Ile Ser Gln Val Gln Lys Thr Asp Pro Ser Asn Glu
                180                 185                 190

Ala Val Thr Val Val Gly Gly His Ser Gly Val Thr Ile Val Pro Leu
                195                 200                 205

Leu Ser Gln Ser Ser His Pro Ser Ile Glu Gly Lys Thr Arg Asp Glu
                210                 215                 220

Leu Val Asn Arg Ile Gln Phe Gly Gly Asp Glu Val Val Lys Ala Lys
225                 230                 235                 240

Asp Gly Ala Gly Ser Ala Thr Leu Ser Met Ala Met Ala Gly Ala Arg
                245                 250                 255

Met Ala Glu Ser Leu Leu Lys Ala Ala Gln Gly Glu Lys Gly Val Val
                260                 265                 270

Glu Pro Thr Phe Val Asp Ser Pro Leu Tyr Lys Asp Gln Gly Val Asp
                275                 280                 285

Phe Phe Ala Ser Lys Val Glu Leu Gly Pro Asn Gly Val Glu Lys Ile
                290                 295                 300

Leu Pro Val Gly Gln Val Asn Ala Tyr Glu Glu Lys Leu Leu Glu Ala
305                 310                 315                 320

Cys Leu Gly Asp Leu Lys Lys Asn Ile Gln Lys Gly Ile Asp Phe Val
                325                 330                 335

Lys Ala Asn Pro
                340
```